United States Patent
Ross et al.

(10) Patent No.: US 7,429,450 B2
(45) Date of Patent: Sep. 30, 2008

(54) HIP1 CANCER MARKERS

(75) Inventors: Theodora Ross, Ann Arbor, MI (US); Ikuko Mizukami, Ann Arbor, MI (US); Dinesh Rao, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 729 days.

(21) Appl. No.: 10/007,047

(22) Filed: Dec. 6, 2001

(65) Prior Publication Data
US 2003/0124533 A1    Jul. 3, 2003

Related U.S. Application Data

(60) Provisional application No. 60/335,276, filed on Nov. 15, 2001.

(51) Int. Cl.
*C12Q 1/68* (2006.01)
(52) U.S. Cl. .......................................................... 435/6
(58) Field of Classification Search ...................... 435/6; 436/64
See application file for complete search history.

(56) References Cited

U.S. PATENT DOCUMENTS 6,235,879 B1    5/2001    Kalchman et al. ........... 530/350
6,794,501 B2 *  9/2004    Chen et al. .................. 536/23.1

FOREIGN PATENT DOCUMENTS

WO    WO 0055633 A2 *    9/2000
WO    WO 00/78813        12/2000

OTHER PUBLICATIONS

Tockman et al (Cancer Res., 1992, 52:2711s-2718s).*
Slamon et al. (Science vol. 235, Jan. 1987, pp. 177-182).*
Abate-Shen and Shen, Genes Dev. 14:2410 [2000].
Ruijter et al., Endocr Rev. 20:22 [1999].
Kalchman et al., Nat.Genet. 16:44 [1997].
Wanker et al., Hum. Mol. Genet. 6:487 [1997].
Metzler et al., J. Biol. Chem. 276:39271 [2001].
Mishra et al., J. Biol. Chem. 276:46230 [2001].
Rao et al., Mol Cell Biol. 21:7796 [2001].
Waelter et al., Hum. Mol. Genet. 10:1807 [2001].
Itoh et al., Science 291:1047 [2001].
Ford et al., Science 291:1051 [2001].
Kim et al., Curr Opin. Oncol. 13:506 [2001].
Davies et al., Nature 417:949 [2002].
Bos, Cancer Res. 49:4682 [1989].
Vieira et al., Science 274:2086 [1996].
DiFiore et al., Cell 106:1 [2001].
Monks et al., J. Natl. Cancer inst., 83:757 [1991].
Ross et al., Blood 91:4419 [1998].
Greenberg et al., PNAS 92:3439 [1995].
Perrone et al., J. Natl. Cancer Inst., 92:937 [2000].
Rao et al., J. Clin Invest. 110:351 [2002].
Saint-Dic et al., J. Biol. Chem. 276:21192 [2001].
DiFiore et al., Cell 51:1063 [1987].
Daley et al., PNAS 85:9312 [1988].
DiFiore et al. Science 237:178 [1987].
Yarden et al., Nat. Rev. Mol. Cell. Biol. 2:127 [2001].
Confalonieri et al., J. Cell. Biol. 150:905 [2000].
Fazioli et al., Mol. Cell. Biol. 13:5814 [1993].

* cited by examiner

*Primary Examiner*—Brandon Fetterolf
(74) *Attorney, Agent, or Firm*—Casimir Jones, S.C.

(57) ABSTRACT

The present invention relates to compositions and methods for cancer diagnostics and therapeutics, including but not limited to, HIP1 cancer markers. In particular, the present invention provides compositions and methods of using HIP1 in the diagnosis and treatment of epithelial cancers. The present invention thus provides improved compositions and methods for diagnosing and treating some of the most common cancers (e.g., prostate and colon cancers). The present invention additionally provides drugs active against HIP1 and methods for screening for such drugs.

4 Claims, 22 Drawing Sheets

Figure 3
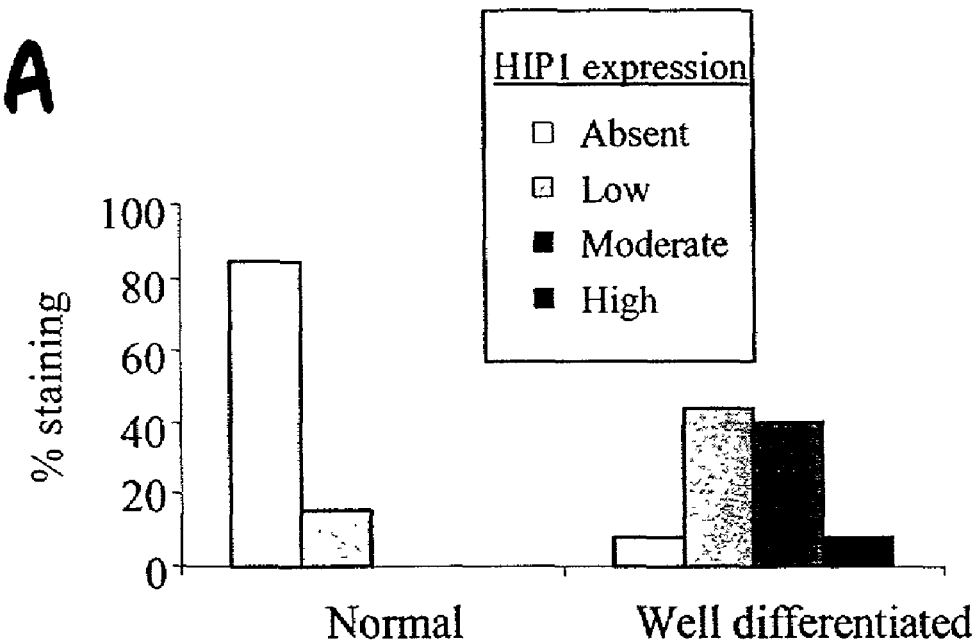
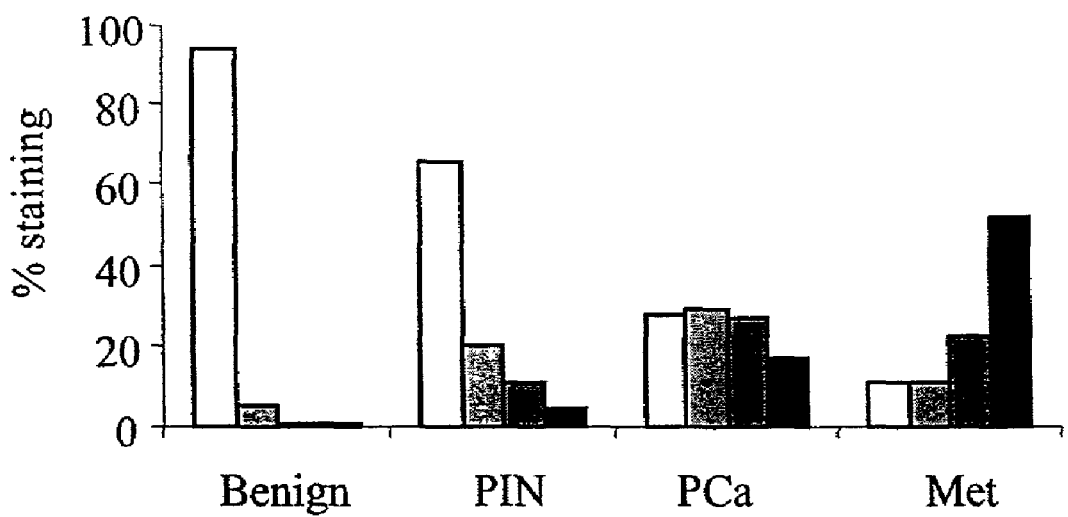

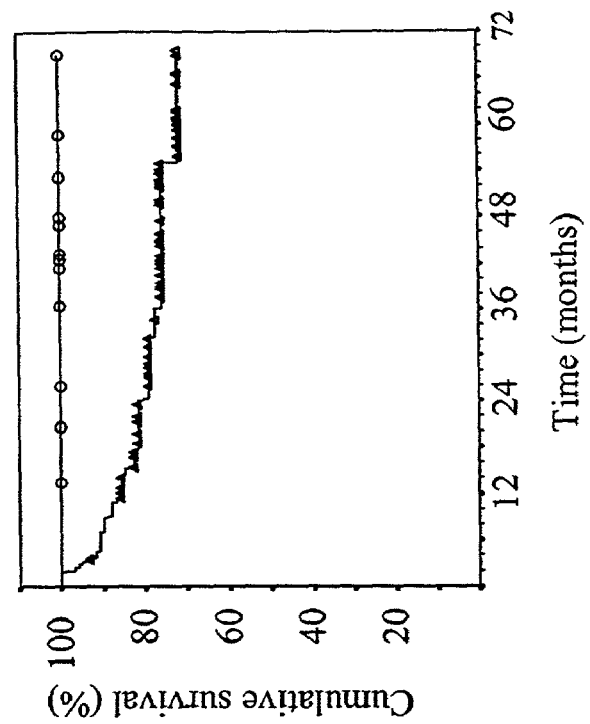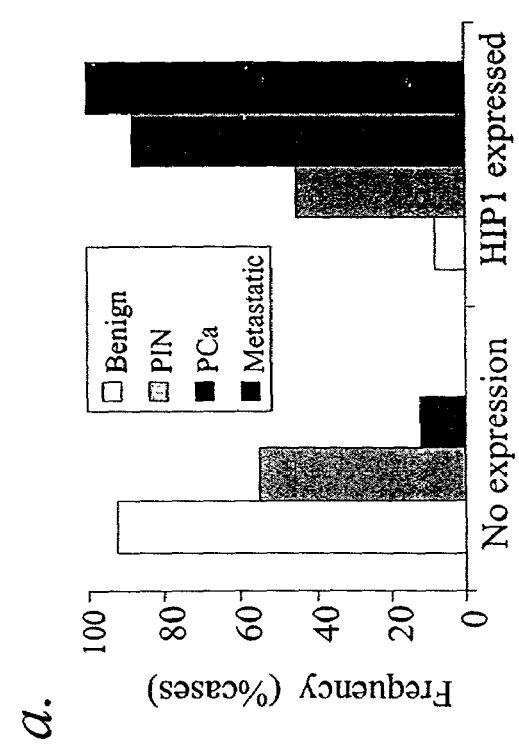
Figure 4

Figure 5

|  |  | HIP1 expression |  |  |  | Total |
|---|---|---|---|---|---|---|
|  |  | Absent | Low | Moderate | High |  |
| ID # | 21 | 6 |  |  |  | 6 |
|  | 22 |  | 2 |  |  | 2 |
|  | 23 | 1 | 1 | 1 |  | 3 |
|  | 25 | 1 | 3 |  |  | 4 |
|  | 26 |  | 2 | 1 |  | 3 |
|  | 31 |  |  | 3 | 1 | 4 |
|  | 32 |  | 1 | 2 | 1 | 4 |
|  | 33 |  |  |  | 2 | 2 |
|  | 38 | 1 |  | 1 | 4 | 6 |
|  | 43 |  | 2 | 2 | 1 | 5 |
|  | 44 | 2 | 2 |  |  | 4 |
|  | 45 |  | 2 |  |  | 2 |
|  | 53 |  | 1 | 2 | 1 | 4 |
|  | 56 |  |  | 2 |  | 2 |
|  | 58 |  |  | 3 | 1 | 4 |
|  | 62 | 1 |  | 1 | 2 | 4 |
|  | 63 |  |  | 5 | 1 | 6 |
|  | 65 | 1 | 1 | 1 | 2 | 5 |
|  | 66 | 1 | 1 | 1 |  | 3 |
|  | 67 | 2 | 1 |  | 1 | 4 |
|  | 70 | 2 | 1 | 2 |  | 5 |
|  | 73 |  | 1 | 6 |  | 7 |
|  | 75 | 2 |  |  |  | 2 |
|  | 76 | 1 | 3 | 1 |  | 5 |
|  | 77 | 3 | 1 |  |  | 4 |
|  | 78 | 1 | 2 |  |  | 3 |
|  | 82 | 1 | 2 |  |  | 3 |
|  | 83 | 1 | 1 | 1 | 3 | 6 |
|  | 84 | 2 | 1 | 1 | 2 | 6 |
|  | 85 | 1 | 3 | 1 |  | 5 |
|  | 89 | 1 | 1 | 3 | 1 | 6 |
|  | 91 |  |  | 4 |  | 4 |
|  | 92 | 1 | 1 | 1 |  | 3 |
|  | 93 |  | 1 | 2 | 2 | 5 |
|  | 96 | 2 | 1 | 1 | 2 | 6 |
|  | 97 | 1 | 2 | 1 |  | 4 |
|  | 99 |  |  | 2 | 2 | 4 |
|  | 101 |  | 2 | 4 |  | 6 |
|  | 102 | 4 |  |  | 1 | 5 |
|  | 103 |  | 4 |  |  | 4 |
|  | 105 |  | 2 | 1 |  | 3 |
|  | 106 | 1 | 1 |  | 1 | 3 |
|  | 108 |  | 1 | 2 | 3 | 6 |
|  | 109 |  | 1 | 5 |  | 6 |
|  | 110 | 3 |  |  |  | 3 |
|  | 111 | 4 | 1 |  |  | 5 |
|  | 113 | 2 |  | 2 |  | 4 |
|  | 114 | 2 |  |  |  | 2 |
|  | 115 |  |  |  | 2 | 2 |
|  | 117 |  |  | 2 |  | 2 |

|  |  | HIP1 expression |  |  |  | Total |
|---|---|---|---|---|---|---|
|  |  | Absent | Low | Moderate | High |  |
| ID # | 118 |  | 1 | 3 |  | 4 |
|  | 119 |  | 2 | 3 | 2 | 7 |
|  | 123 | 3 | 3 | 1 |  | 7 |
|  | 125 | 4 | 2 |  |  | 6 |
|  | 127 | 3 | 1 |  |  | 4 |
|  | 128 |  |  | 1 | 3 | 4 |
|  | 129 | 3 | 1 |  |  | 4 |
|  | 131 | 1 | 1 |  |  | 2 |
|  | 132 |  |  | 3 | 1 | 4 |
|  | 141 |  |  | 2 | 2 | 4 |
|  | 142 | 2 | 3 |  |  | 5 |
|  | 144 | 1 | 3 | 2 | 1 | 7 |
|  | 145 | 2 |  |  |  | 2 |
|  | 153 |  | 1 | 1 |  | 2 |
|  | 154 | 2 |  |  |  | 2 |
|  | 155 |  |  |  | 4 | 4 |
|  | 159 | 4 | 2 |  |  | 6 |
|  | 161 | 2 |  |  |  | 2 |
|  | 162 | 1 | 1 | 1 |  | 3 |
|  | 164 |  |  | 1 | 3 | 4 |
|  | 165 |  | 4 | 2 |  | 6 |
|  | 169 |  | 2 |  |  | 2 |
|  | 170 | 3 | 2 | 1 |  | 6 |
|  | 171 |  |  | 2 |  | 2 |
|  | 172 | 2 |  |  |  | 2 |
|  | 173 | 3 |  | 1 |  | 4 |
|  | 175 | 3 |  |  |  | 3 |
|  | 177 | 4 | 2 |  |  | 6 |
|  | 178 | 2 | 1 |  |  | 3 |
|  | 179 | 3 | 1 |  |  | 4 |
|  | 180 | 1 |  |  | 3 | 4 |
|  | 181 | 4 |  |  |  | 4 |
|  | 182 | 2 |  |  |  | 2 |
|  | 183 |  | 2 |  |  | 2 |
|  | 186 |  | 4 |  |  | 4 |
|  | 194 | 4 | 1 |  |  | 5 |
|  | 194 | 2 | 1 |  |  | 3 |
|  | 195 | 1 | 5 | 1 |  | 7 |
|  | 199 |  | 1 | 1 | 1 | 3 |
|  | 204 |  | 3 | 1 |  | 4 |
|  | 205 |  |  | 2 | 2 | 4 |
|  | 206 |  | 6 |  |  | 6 |
|  | 207 |  | 4 |  |  | 4 |
|  | 208 |  |  | 3 | 1 | 4 |
|  | 209 |  |  | 2 | 3 | 5 |
|  | 212 | 1 | 4 | 1 | 3 | 9 |
|  | 213 | 2 | 3 | 2 |  | 7 |
|  | 214 |  | 1 | 1 | 3 | 5 |
|  | 217 |  | 1 | 2 | 3 | 6 |
|  | 218 | 1 | 6 |  |  | 7 |

Figure 5 continued

|  |  | HIP1 expression | | | | Total |
|---|---|---|---|---|---|---|
|  |  | Absent | Low | Moderate | High |  |
| ID # | 220 |  | 1 |  | 5 | 6 |
|  | 225 |  | 1 | 3 |  | 4 |
|  | 228 |  |  | 3 |  | 3 |
|  | 229 | 1 |  | 2 | 1 | 4 |
|  | 230 | 2 |  |  |  | 2 |
|  | 231 |  |  | 2 | 1 | 3 |
|  | 234 |  |  | 2 |  | 2 |
|  | 235 |  | 3 | 1 |  | 4 |
|  | 236 | 2 | 3 |  |  | 5 |
|  | 237 | 4 | 1 |  |  | 5 |
|  | 238 | 2 |  |  |  | 2 |
|  | 239 |  | 3 | 2 |  | 5 |
|  | 241 | 2 | 1 | 1 |  | 4 |
|  | 248 |  |  | 2 |  | 2 |
| TOTAL |  | 128 | 136 | 123 | 76 | 463 |

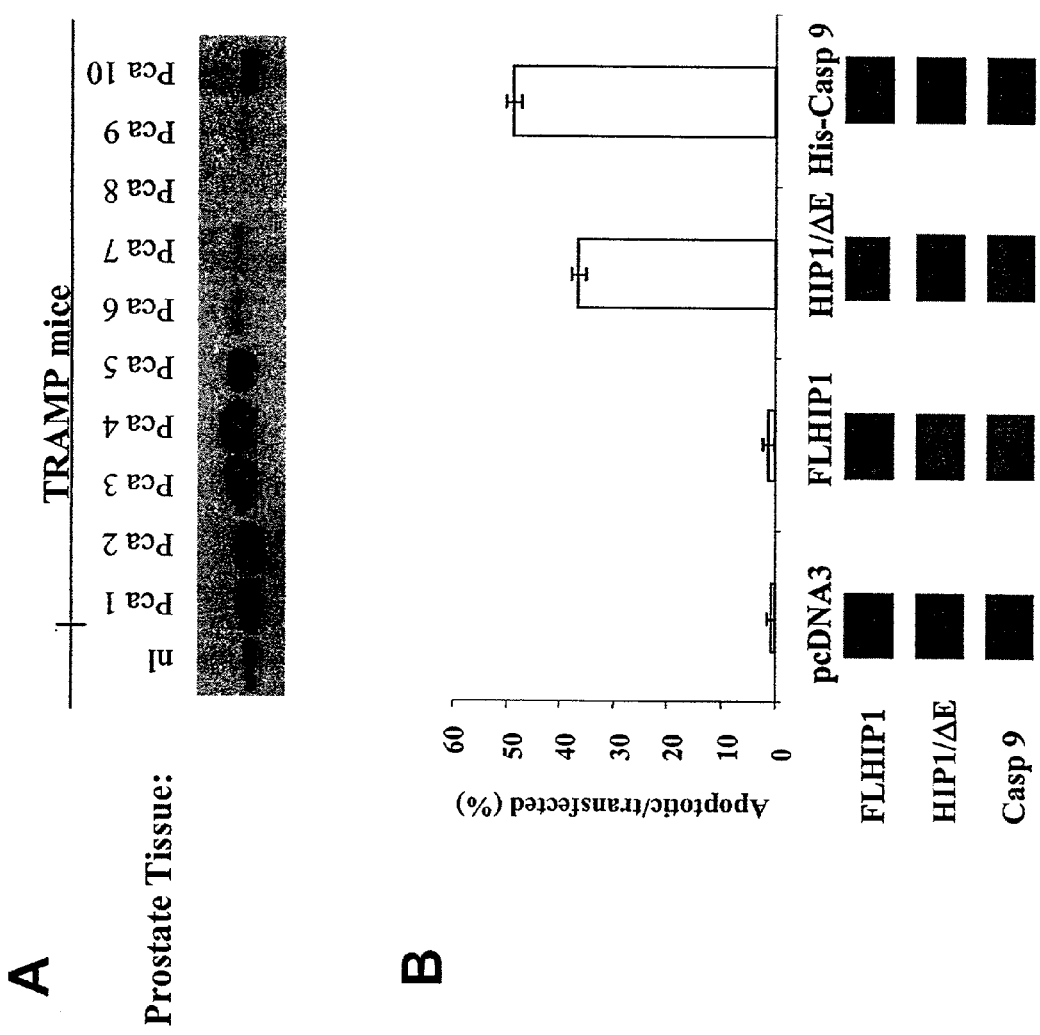

Figure 7
Full length HIP1

```
ccaagcttggtaccccggggcagccgagggcccctgactcggctcctcgcggcgacatggatcggatggc
cagctccatgaagcaggtgcccaacccactgcccaaggtgctgagccggcgcggggtcggcgctgggctgg
aggcggcggagcgcgagagcttcgagcggactcagactgtcagcatcaataaggccattaatacgcaggaa
gtggctgtaaaggaaaaacacgccagaacgtgcatactgggcacccaccatgagaaaggggcacagacctt
ctggtctgttgtcaaccgcctgcctctgtctagcaacgcagtgctctgctggaagttctgccatgtgttcc
acaaactcctccgagatggacacccgaacgtcctgaaggactctctgagatacagaaatgaattgagtgac
atgagcaggatgtggggctacctgagcgagggggtatggccagctgtgcagcatctacctgaaactgctaag
aaccaagatggagtaccacaccaaaaatcccaggttcccaggcaacctgcagatgagtgaccgccagctgg
acgaggctggagaaagtgacgtgaacaacttttcccagttaacagtggagatgtttgactacctggagtgt
gaactcaacctcttccaaacagtattcaactccctggacatgtcccgctctgtgtccgtgacggcagcagg
gcagtgccgcctcgcccgctgatccaggtcatcttggactgcagccacctttatgactacactgtcaagc
ttctcttcaaactccactcctgcctcccagctgacaccctgcaaggccaccgggaccgcttcatggagcag
tttacaaagttgaaagatctgttctaccgctccagcaacctgcagtacttcaagcggctcattcagatccc
ccagctgcctgagaacccacccaacttcctgcgagcctcagccctgtcagaacatatcagccctgtggtgg
tgatccctgcagaggcctcatccccgacagcgagccagtcctagagaaggatgacctcatggacatggat
gcctctcagcagaatttatttgacaacaagtttgatgacatctttggcagttcattcagcagtgatcccctt
caatttcaacagtcaaaatggtgtgaacaaggatgagaaggaccacttaattgagcgactatacagagaga
tcagtggattgaaggcacagctagaaaacatgaagactgagagccagcgggttgtgctgcagctgaagggc
cacgtcagcgagctggaagcagatctggccgagcagcagcacctgcggcagcaggcggccgacgactgtga
attcctgcgggcagaactggacgagctcaggaggcagcgggaggacaccgagaaggctcagcggagcctgt
ctgagatagaaaggaaagctcaagccaatgaacagcgatatagcaagctaaaggagaagtacagcgagctg
gttcagaaccacgctgacctgctgcggaagaatgcagaggtgaccaaacaggtgtccatggccagacaagc
ccaggtagatttggaacgagagaaaaaagagctggaggattcgttggagcgcatcagtgaccagggccagc
ggaagactcaagaacagctggaagttctagagagcttgaagcaggaacttgccacaagccaacgggagctt
caggttctgcaaggcagcctggaaacttctgcccagtcagaagcaaactgggcagccgagttcgccgagct
agagaaggagcgggacagcctggtgagtggcgcagctcatagggaggaggaattatctgctcttcggaaag
aactgcaggacactcagctcaaactggccagcacagaggaatctatgtgccagcttgccaaagaccaacga
aaaatgcttctggtggggtccaggaaggctgcggagcaggtgatacaagacgccctgaaccagcttgaaga
acctcctctcatcagctgcgctgggtctgcagatcacctcctctccacggtcacatccatttccagctgca
tcgagcaactggagaaaagctggagccagtatctggcctgcccagaagacatcagtggacttctccattcc
ataaccctgctggcccacttgaccagcgacgccattgctcatggtgccaccacctgcctcagagccccacc
tgagcctgccgactcactgaccgaggcctgtaagcagtatggcagggaaaccctcgcctacctggcctcc
tggaggaagagggaagccttgagaatgccgacagcacagccatgaggaactgcctgagcaagatcaaggcc
atcggcgaggagctcctgcccaggggactggacatcaagcaggaggagctgggggacctggtggacaagga
gatggcggccacttcagctgctattgaaactgccacggccagaatagaggagatgctcagcaaatcccgag
caggagacacaggagtcaaattggaggtgaatgaaaggatccttggttgctgtaccagcctcatgcaagct
attcaggtgctcatcgtggcctctaaggacctccagagagagattgtggagagcggcaggggtacagcatc
ccctaaagagttttatgccaagaactctcgatggacagaaggacttatctcagcctccaaggctgtgggct
ggggagccactgtcatggtggatgcagctgatctggtggtacaaggcagagggaaatttgaggagctaatg
gtgtgttctcatgaaattgctgctagcacagcccagcttgtggctgcatccaaggtgaaagctgataagga
cagccccaacctagcccagctgcagcaggcctctcggggagtgaaccaggccactgccggcgttgtggcct
caaccatttccggcaaatcacagatcgaagagacagacaacatggacttctcaagcatgacgctgacacag
atcaaacgccaagagatggattctcaggttagggtgctagagctagaaaatgaattgcagaaggagcgtca
aaaactgggagagcttcggaaaaagcactacgagcttgctggtgttgctgagggctgggaagaaggaacag
aggcatctccacctacactgcaagaagtggtaaccgaaaaagaatagagccaaaccaacaccccatatgtc
agtgtaaatccttgttacctatctcgtgtgtgttatttccccagccacaggccaaatccttggagtcccag
gggcagccacaccactgccattacccagtgccgaggacatgcatgacacttccaaagactccctccatagc
gacacccttcctgtttggacccatggatttccactgcttcttatggtggttggttgggttttttggttttg
ttttttttttttaagtttcactcacatagccaactctcccaaagggcacaccctggggctgagtctccag
ggcccccaactgtggtagctccagcgatggtgctgcccaggcctctcggtgctccatctccgcctccaca
ctgaccaagtgctggcccacccagtccatgctccagggtcaggcggagctgctgagtgacagcttcctca
aaaagcagaaggagagtgagtgcctttccctcctaaagctgaatcccggcggaaagcctctgtccgccttt
```

Figure 7 continued

```
acaagggagaagacaacagaaagagggacaagagggttcacacagcccagttcccgtgacgaggctcaaaa
acttgatcacatgcttgaatggagctggtgagatcaacaacactacttccctgccggaatgaactgtccgt
gaatggtctctgtcaagcgggccgtctcccttggcccagagacggagtgtgggagtgattcccaactcctt
tctgcagacgtctgccttggcatcctcttgaataggaagatcgttccaccttctacgcaattgacaaaccc
ggaagatcagatgcaattgctcccatcagggaagaaccctatacttggtttgctacccttagtatttatta
ctaacctcccttaagcagcaacagcctacaaagagatgcttggagcaatcagaacttcaggtgtgactcta
gcaaagctcatctttctgcccggctacatcagccttcaagaatcagaagaaaggccaaggtgctggactgt
tactgacttggatcccaaagcaaggagatcatttggagctcttgggtcagagaaaatgagaaaggacagag
ccagcggctccaactcctttcagccacatgccccaggctctcgctgccctgtggacaggatgaggacagag
ggcacatgaacagcttgccagggatgggcagcccaacagcacttttcctcttctagatggaccccagcatt
taagtgaccttctgatcttgggaaaacagcgtcttccttctttatctatagcaactcattggtggtagcca
tcaagcacttcggaattcctgcagcccgggcggccgctcgagcatgcnntagagggcccta
```

Figure 8
Full length HIP1

MDRMASSMKQVPNPLPKVLSRRGVGAGLEAAERESFERTQTVSINKAINTQEVAVKEKHARTCILGTHHEK
GAQTFWSVVNRLPLSSNAVLCWKFCHVFHKLLRDGHPNVLKDSLRYRNELSDMSRMWGYLSEGYGQLCSIY
LKLLRTKMEYHTKNPRFPGNLQMSDRQLDEAGESDVNNFSQLTVEMFDYLECELNLFQTVFNSLDMSRSVS
VTAAGQCRLAPLIQVILDCSHLYDYTVKLLFKLHSCLPADTLQGHRDRFMEQFTKLKDLFYRSSNLQYFKR
LIQIPQLPENPPNFLRASALSEHISPVVVIPAEASSPDSEPVLEKDDLMDMDASQQNLFDNKFDDIFGSSF
SSDPFNFNSQNGVNKDEKDHLIERLYREISGLKAQLENMKTESQRVVLQLKGHVSELEADLAEQQHLRQQA
ADDCEFLRAELDELRRQREDTEKAQRSLSEIERKAQANEQRYSKLKEKYSELVQNHADLLRKNAEVTKQVS
MARQAQVDLEREKKELEDSLERISDQGQRKTQEQLEVLESLKQELATSQRELQVLQGSLETSAQSEANWAA
EFAELEKERDSLVSGAAHREEELSALRKELQDTQLKLASTEESMCQLAKDQRKMLLVGSRKAAEQVIQDAL
NQLEEPPLISCAGSADHLLSTVTSISSCIEQLEKSWSQYLACPEDISGLLHSITLLAHLTSDAIAHGATTC
LRAPPEPADSLTEACKQYGRETLAYLASLEEEGSLENADSTAMRNCLSKIKAIGEELLPRGLDIKQEELGD
LVDKEMAATSAAIETATARIEEMLSKSRAGDTGVKLEVNERILGCCTSLMQAIQVLIVASKDLQREIVESG
RGTASPKEFYAKNSRWTEGLISASKAVGWGATVMVDAADLVVQGRGKFEELMVCSHEIAASTAQLVAASKV
KADKDSPNLAQLQQASRGVNQATAGVVASTISGKSQIEETDNMDFSSMTLTQIKRQEMDSQVRVLELENEL
QKERQKLGELRKKHYELAGVAEGWEEGTEASPPTLQEVVTEKE*SQTNTPYVSVNPCYLSRVCYFPSHRPN
PWSPRGSHTTAITQCRGHA*HFQRLPP*RHPFCLDPWISTASYGGWLGFLVLFFFFKFHSHSQLSQRAHPW
G*VSRAPQLW*LQRWCCPGLSVLHLRLHTDQVLAHPVHAPGSGGAAE*QLSSKSRRRVSAFPS*S*IPAES
LCPPLQGRRQQKEGQEGSHSPVPVTRLKNLITCLNGAGEINNTTSLPE*TVREWSLSSGPSPLAQRRSVGV
IPNSFLQTSALASS*IGRSFHLLRN*QTRKIRCNCSHQGRTLYLVCYP*YLLLTSLKQQQPTKRCLEQSEL
QV*L*QSSSFCPATSAFKNQKKGQGAGLLLTWIPKQGDHLELLGQRK*ERTEPAAPTPFSHMPQALAALWT
G*GQRAHEQLARDGQPNSTFPLLDGPQHLSDLLILGKQRLPSLSIATHWW*PSSTSEFLQPGRPLEHAXEG
P (* are stop sequences)

Figure 9
Delta ENTH

```
gttaacagtggagatgtttgactacctggagtgtgaactcaacctcttccaaacagtattcaactccctgg
acatgtcccgctctgtgtccgtgacggcagcagggcagtgccgcctcgcccgctgatccaggtcatcttg
gactgcagccacctttatgactacactgtcaagcttctcttcaaactccactcctgcctcccagctgacac
cctgcaaggccaccgggaccgcttcatggagcagtttacaaagttgaaagatctgttctaccgctccagca
acctgcagtacttcaagcggctcattcagatccccagctgcctgagaacccacccaacttcctgcgagcc
tcagccctgtcagaacatatcagccctgtggtggtgatccctgcagaggcctcatccccgacagcgagcc
agtcctagagaaggatgacctcatggacatggatgcctctcagcagaatttatttgacaacaagtttgatg
acatctttggcagttcattcagcagtgatcccttcaatttcaacagtcaaaatggtgtgaacaaggatgag
aaggaccacttaattgagcgactatacagagagatcagtggattgaaggcacagctagaaaacatgaagac
tgagagccagcgggttgtgctgcagctgaagggccacgtcagcgagctggaagcagatctggccgagcagc
agcacctgcggcagcaggcggccgacgactgtgaattcctgcgggcagaactggacgagctcaggaggcag
cggagggacaccgagaaggctcagcggagcctgtctgagatagaaggaaagctcaagccaatgacagcg
atatagcaagctaaaggagaagtacagcgagctggttcagaaccacgctgacctgctgcggaagaatgcag
aggtgaccaaacaggtgtccatggccagacaagcccaggtagatttggaacgagagaaaaaagagctggag
gattcgttggagcgcatcagtgaccagggccagcggaagactcaagaacagctggaagttctagagagctt
gaagcaggaacttgccacaagccaacgggagcttcaggttctgcaaggcagcctggaaacttctgcccagt
cagaagcaaactgggcagccgagttcgccgagctagagaaggagcgggacagcctggtgagtggcgcagct
catagggaggaggaattatctgctcttcggaaagaactgcaggacactcagctcaaactggccagcacaga
ggaatctatgtgccagcttgccaaagaccaacgaaaaatgcttctggtggggtccaggaaggctgcggagc
aggtgatacaagacgccctgaaccagcttgaagaacctcctctcatcagctgcgctgggtctgcagatcac
ctcctctccacggtcacatccatttccagctgcatcgagcaactggagaaaagctggagccagtatctggc
ctgcccagaagacatcagtggacttctccattccataaccctgctggcccacttgaccagcgacgccattg
ctcatggtgccaccacctgcctcagagccccacctgagcctgccgactcactgaccgaggcctgtaagcag
tatggcagggaaaccctcgcctacctggcctcccctggaggaagagggaagccttgagaatgccgacagcac
agccatgaggaactgcctgagcaagatcaaggccatcggcgaggagctcctgcccaggggactggacatca
agcaggaggagctggggggacctggtggacaaggagatggcggccacttcagctgctattgaaactgccacg
gccagaatagaggagatgctcagcaaatcccgagcaggagacacaggagtcaaattggaggtgaatgaaag
gatccttggttgctgtaccagcctcatgcaagctattcaggtgctcatcgtggcctctaaggacctccaga
gagagattgtggagagcggcaggggtacagcatcccctaaagagttttatgccaagaactctcgatggaca
gaaggacttatctcagcctccaaggctgtgggctggggagccactgtcatggtggatgcagctgatctggt
ggtacaaggcagagggaaatttgaggagctaatggtgtgttctcatgaaattgctgctagcacagcccagc
ttgtggctgcatccaaggtgaaagctgataaggacagccccaacctagcccagctgcagcaggcctctcgg
ggagtgaaccaggccactgccggcgttgtggcctcaaccatttccggcaaatcacagatcgaagagacaga
caacatggacttctcaagcatgacgctgacacagatcaaacgccaagagatggattctcaggttagggtgc
tagagctagaaaatgaattgcagaaggagcgtcaaaaactgggagagcttcggaaaaagcactacgagctt
gctggtgttgctgagggctgggaagaaggaacagaggcatctccacctacactgcaagaagtggtaaccga
aaaagaatagagccaaaccaacaccccatatgtcagtgtaaatccttgttacctatctcgtgtgtgttatt
tccccagccacaggccaaatccttggagtcccaggggcagccacaccactgccattacccagtgccgagga
catgcatgacacttccaaagactccctccatagcgacacccttctgtttggacccatggatttccactgc
ttcttatggtggttggttgggttttttggttttgtttttttttttaagtttcactcacatagccaactct
cccaaagggcacacccctggggctgagtctccagggcccccaactgtggtagctccagcgatggtgctgc
ccaggcctctcggtgctccatctccgcctccacactgaccaagtgctggcccacccagtccatgctccagg
gtcaggcggagctgctgagtgacagctttcctcaaaaagcagaaggagagtgagtgcctttccctcctaaa
gctgaatcccggcggaaagcctctgtccgcctttacaagggagaagacaacagaaagagggacaagagggt
tcacacagcccagttcccgtgacgaggctcaaaaacttgatcacatgcttgaatggagctggtgagatcaa
caacactacttccctgccggaatgaactgtccgtgaatggtctctgtcaagcgggccgtctcccttggccc
agagacggagtgtgggagtgattcccaactcctttctgcagacgtctgccttggcatcctcttgaatagga
agatcgttccaccttctacgcaattgacaaacccggaagatcagatgcaattgctcccatcagggaagaac
cctatacttggtttgctacccttagtatttattactaacctcccttaagcagcaacagcctacaaagagat
gcttggagcaatcagaacttcaggtgtgactctagcaaagctcatctttctgcccggctacatcagccttc
```

Figure 9 continued

```
aagaatcagaagaaaggccaaggtgctggactgttactgacttggatcccaaagcaaggagatcatttgga
gctcttgggtcagagaaaatgagaaaggacagagccagcggctccaactcctttcagccacatgccccagg
ctctcgctgccctgtggacaggatgaggacagagggcacatgaacagcttgccagggatgggcagcccaac
agcactttcctcttctagatggaccccagcatttaagtgaccttctgatcttgggaaaacagcgtcttcc
ttctttatctatagcaactcattggtggtagccatcaagcacttcggaattcctgcagcccgggcggccgc
tcgagc
```

Figure 10
Delta ENTH

```
MFDYLECELNLFQTVFNSLDMSRSVSVTAAGQCRLAPLIQVILDCSHLYDYTVKLLFKLHSCLPADTLQGH
RDRFMEQFTKLKDLFYRSSNLQYFKRLIQIPQLPENPPNFLRASALSEHISPVVVIPAEASSPDSEPVLEK
DDLMDMDASQQNLFDNKFDDIFGSSFSSDPFNFNSQNGVNKDEKDHLIERLYREISGLKAQLENMKTESQR
VVLQLKGHVSELEADLAEQQHLRQQAADDCEFLRAELDELRRQREDTEKAQRSLSEIERKAQANEQRYSKL
KEKYSELVQNHADLLRKNAEVTKQVSMARQAQVDLEREKKELEDSLERISDQGQRKTQEQLEVLESLKQEL
ATSQRELQVLQGSLETSAQSEANWAAEFAELEKERDSLVSGAAHREEELSALRKELQDTQLKLASTEESMC
QLAKDQRKMLLVGSRKAAEQVIQDALNQLEEPPLISCAGSADHLLSTVTSISSCIEQLEKSWSQYLACPED
ISGLLHSITLLAHLTSDAIAHGATTCLRAPPEPADSLTEACKQYGRETLAYLASLEEEGSLENADSTAMRN
CLSKIKAIGEELLPRGLDIKQEELGDLVDKEMAATSAAIETATARIEEMLSKSRAGDTGVKLEVNERILGC
CTSLMQAIQVLIVASKDLQREIVESGRGTASPKEFYAKNSRWTEGLISASKAVGWGATVMVDAADLVVQGR
GKFEELMVCSHEIAASTAQLVAASKVKADKDSPNLAQLQQASRGVNQATAGVVASTISGKSQIEETDNMDF
SSMTLTQIKRQEMDSQVRVLELENELQKERQKLGELRKKHYELAGVAEGWEEGTEASPPTLQEVVTEKE*S
QTNTPYVSVNPCYLSRVCYFPSHRPNPWSPRGSHTTAITQCRGHA*HFQRLPP*RHPFCLDPWISTASYGG
WLGFLVLFFFFKFHSHSQLSQRAHPWG*VSRAPQLW*LQRWCCPGLSVLHLRLHTDQVLAHPVHAPGSGGA
AE*QLSSKSRRRVSAFPS*S*IPAESLCPPLQGRRQQKEGQEGSHSPVPVTRLKNLITCLNGAGEINNTTS
LPE*TVREWSLSSGPSPLAQRRSVGVIPNSFLQTSALASS*IGRSFHLLRN*QTRKIRCNCSHQGRTLYLV
CYP*YLLLTSLKQQQPTKRCLEQSELQV*L*QSSSFCPATSAFKNQKKGQGAGLLLTWIPKQGDHLELLGQ
RK*ERTEPAAPTPFSHMPQALAALWTG*GQRAHEQLARDGQPNSTFPLLDGPQHLSDLLILGKQRLPSLSI
ATHWW*PSSTSEFLQPGRPLEH
```

(* are stop sequences)

Domain Structure of HIP1

Rescue of apoptosis caused by ΔE with FLHIP1

Vector Construction Strategy for conditional HIP1 knock-out

Figure 17

```
       -173  GGGCCGAGCCAGCGGAGGGGCTCCTGAAGGGGCGGGGGCGGGCGGGGAAGCCGT
       -119  TCGGCGAGGGGCGGGGTCTCTGGAAGACTGGCAGAACTCACAGCCAATGGCAGGC
        -64  GGGAGCCGTCCCGTTAGCGCCGGATCCCCGCGGGTAGGGCGGGGCGGGCGGCGCC
        -10  GTGGGGATCC
exon 1    0  CGGGGCAGCCGAGGGCCCCTGACTCGGCTCCTCGCGGCGACATGGATCGGATGGCCA
         57  GCTCCATGAAGCAGGTGCCCAACCCACTGCCCAAGGTGCTGAGCCGGCGCGGGGTCG
        114  GCGCTGGGCTGGAGGCGGCGGAGCGCGAGAGCTTCGAGCGGAC TCAGGT......
             ......TCAG
exon 2  161  ACTGTCAGCATCAATAAGGCCATTAATACGCAGGAAAGTGGCTGTAAAGGAAAAACATGCC
        222  AG
```

Deletion of the HIP1/PDGFβR knock-in ES cell allele

HIP1 CANCER MARKERS

This application claims priority to Provisional Patent Application Ser. No. 60/335,276, filed Nov. 15,2001.

This invention was made with government support under Grant Nos. KO8 CA76025-05 and RO1 CA82363-02, awarded by the National Institutes of Health. The Government has certain rights in the invention.

FIELD OF THE INVENTION

The present invention relates to compositions and methods for cancer diagnostics, including but not limited to, HIP1 cancer markers. In particular, the present invention provides compositions and methods of using HIP1 in the diagnosis and treatment of epithelial cancers. The present invention further provides methods of screening potential therapeutic compounds for HIP1 inhibitory properties.

BACKGROUND OF THE INVENTION

Most forms of cancer do not have diagnostic screening tests available. For the cancers that do have screening tests available, the tests are frequently invasive, expensive, and lack strong diagnostic utility.

For example, afflicting one out of nine men over age 65, prostate cancer (PCA) is a leading cause of male cancer-related death, second only to lung cancer (Abate-Shen and Shen, Genes Dev 14:2410 [2000]; Ruijter et al., Endocr Rev, 20:22 [1999]). The American Cancer Society estimates that about 184,500 American men will be diagnosed with prostate cancer in 2001 and 39,200 will die.

Prostate cancer is typically diagnosed with a digital rectal exam and/or prostate specific antigen (PSA) screening. An elevated PSA level can indicate the presence of PCA. PSA is used as a marker for prostate cancer because it is essentially restricted to prostate cells. A healthy prostate will produce a stable amount—typically below 4 nanograms per milliliter, or a PSA reading of "4" or less—whereas cancer cells produce escalating amounts that correspond with the severity of the cancer. A level between 4 and 10 may raise a doctor's suspicion that a patient has prostate cancer, while amounts above 50 may show that the tumor has spread elsewhere in the body.

The advent of prostate specific antigen (PSA) screening has led to earlier detection of PCA and significantly reduced PCA-associated fatalities. Elevated serum PSA levels, however, are often detected in patients with non-malignant conditions such as benign prostatic hyperplasia (BPH), and provide little information about the aggressiveness of the cancer detected.

In addition, colon cancer, which is the second most frequently diagnosed malignancy in the United States as well as the second most common cause of cancer death, lacks an effective screening assay. The prognosis of colon cancer is clearly related to the degree of penetration of the tumor through the bowel wall and the presence or absence of nodal involvement, thus making early diagnosis very important for long-term survival.

A fecal occult blood test (FOBT) is a test used to check for hidden blood in the stool. Sometimes cancers or polyps can bleed, and FOBT is used to detect small amounts of bleeding. In addition, screening tests (such as a rectal examination, proctoscopy, and colonoscopy) may be done regularly in patients who are at high risk of colon cancer or who have a positive FOBT result. The proctoscopy examination finds about half of all colon and rectal cancers. After treatment, a blood test (to measure amounts of carcinoembryonic antigen or CEA in the blood) and x-rays may be done to screen for recurrence. CEA is a serum glycoprotein frequently used in the management of patients with colon cancer. However, a review of the use of this tumor marker suggests that CEA is not a valuable screening test for colorectal cancer due to the large numbers of false-positive and false-negative reports.

Thus, development of additional serum and tissue biomarkers specific to cancer such and prostate and colon are needed to supplement the currently available screening methods.

SUMMARY OF THE INVENTION

The present invention relates to compositions and methods for cancer diagnostics, including but not limited to, HIP1 cancer markers. In particular, the present invention provides compositions and methods of using HIP1 in the diagnosis and treatment of epithelial cancers. The present invention further provides methods of screening potential therapeutic compounds for HIP1 inhibitory properties.

Accordingly, in some embodiments, the present invention provides an antibody that specifically binds to HIP1 but does not specifically bind to the normal epithelium of prostate or colon. In some embodiments, the antibody binds to the cancerous epithelium of colon or prostate but does not bind to the normal epithelium of prostate or colon. In some embodiments, the antibody is a monoclonal antibody. In some embodiments, the monoclonal antibody has substantially the same properties as antibodies secreted by a hybridoma selected from the group consisting of those deposited as ATCC numbers PTA-3901, PTA-3902 and PTA-4071. In some embodiments, the monoclonal antibody is secreted by a hybridoma with ATCC deposit number PTA-3901. In other embodiments, the monoclonal antibody is secreted by a hybridoma with ATCC deposit number PTA-3902. In still further embodiments, the monoclonal antibody specifically binds to HIP1 protein with low background binding. In yet other embodiments, the monoclonal antibody binds to human and mouse HIP1.

The present invention also provides a method for detecting cancer, comprising providing a sample from a subject suspected of having cancer; and detecting the presence or absence of HIP1 in the sample. In some embodiments, the presence of HIP1 in said sample is indicative of cancer in the subject. In some embodiments, the cancer is selected from the group consisting of prostate cancer and colon cancer. In some embodiments, the sample is a tumor sample. In other embodiments, the sample is a tissue sample. In some embodiments, the tissue sample is selected from the group consisting of prostate tissue and colon tissue. In other embodiments, the sample is selected from the group consisting of serum, plasma, blood, and urine. In some embodiments, detecting HIP1 comprises detecting the presence of HIP1 mRNA. In some such embodiments, detecting the presence of HIP1 mRNA comprises exposing the HIP1 mRNA to a nucleic acid probe complementary to at least a portion of the HIP1 mRNA. In some embodiments, detecting the presence of HIP1 mRNA comprises a detection assay selected from the group consisting of a Northern blot, in situ hybridization, reverse-transcriptase polymerase chain reaction, and microarray analysis. In other embodiments, detecting the presence of HIP1 comprises detecting the presence of a HIP1 polypeptide. In some embodiments, detecting the presence of a HIP1 polypeptide comprises exposing the HIP1 polypeptide to an antibody that specifically binds to HIP1 but does not specifically bind to the normal epithelium of prostate or colon and detecting the binding of the antibody to said HIP1 polypeptide. In some embodiments, the antibody is a monoclonal antibody. In some embodiments, the monoclonal antibody has substantially the same properties as antibodies secreted by a hybridoma selected from the group consisting of those deposited as ATCC numbers PTA-3901, PTA-3902 and PTA-4071. In some embodiments, the method further comprises the step of providing a prognosis to the subject.

The present invention additionally provides a method for characterizing tissue in a subject, comprising providing a tissue sample from a subject, wherein the tissue is selected from the group consisting of colon and prostate tissue; and detecting the presence or absence of HIP1 in the sample, thereby characterizing the tissue sample. In some embodiments, the tissue is tumor tissue. In other embodiments, the tissue is biopsy tissue. In some embodiments, detecting HIP1 comprises detecting the presence of HIP1 mRNA. In some embodiments, detecting the presence of HIP1 mRNA comprises exposing the HIP1 mRNA to a nucleic acid probe complementary to at least a portion of the HIP1 mRNA. In some embodiments, detecting the presence of HIP1 mRNA comprises a detection assay selected from the group consisting of a Northern blot, in situ hybridization, reverse-transcriptase polymerase chain reaction, and microarray analysis. In other embodiments, detecting the presence of HIP1 comprises detecting the presence of a HIP1 polypeptide. In some embodiments, detecting the presence of a HIP1 polypeptide comprises exposing the HIP1 polypeptide to an antibody that specifically binds to HIP1 but does not specifically bind to the normal epithelium of prostate or colon and detecting the binding of the antibody to the HIP1 polypeptide. In some embodiments, the antibody is a monoclonal antibody. In some embodiments, the monoclonal antibody has substantially the same properties as antibodies secreted by a hybridoma selected from the group consisting of those deposited as ATCC numbers PTA-3901, PTA-3902 and PTA-4071. In some embodiments, the tissue sample is a post-surgical prostate tumor tissue sample and the method further comprises the step of identifying a risk of prostate specific antigen failure based on detecting the presence or absence of HIP1. In other embodiments, the tissue sample is prostate tumor tissue and characterizing comprises identifying a stage of prostate cancer in the prostate tumor tissue. In some embodiments, the stage is selected from the group consisting of high-grade prostatic intraepithelial neoplasia, benign prostatic hyperplasia, prostate carcinoma, and metastatic prostate carcinoma. In other embodiments, the tissue sample is prostate tumor tissue and the method further comprises the step of identifying the risk of the tumor metastasizing based on detecting the presence of HIP1. In still further embodiments, the tissue sample is post-surgical prostate tumor tissue and the method further comprises the step of identifying the risk of the tumor recurring based on detecting the presence of HIP1.

The present invention additionally provides a kit for characterizing cancer in a subject, comprising a reagent that specifically detects the presence of absence of expression of HIP1; and instructions for using the kit for characterizing cancer in the subject. In some embodiments, the reagent comprises an antibody that specifically binds to HIP1 but does not specifically bind to the normal epithelium of prostate or colon. In some embodiments, the antibody is a monoclonal antibody. In some embodiments, the monoclonal antibody has substantially the same properties as antibodies secreted by a hybridoma selected from the group consisting of those deposited as ATCC numbers PTA-3901, PTA-3902 and PTA-4071. In other embodiments, the reagent comprises a nucleic acid probe that specifically binds to a HIP1 mRNA. In some embodiments, the instructions comprise instructions required by the United States Food and Drug Administration for use in in vitro diagnostic products.

The present invention also provides a method of screening compounds, comprising providing an epithelial cell sample; and one or more test compounds; and contacting the epithelial cell sample with the test compound; and detecting a change in HIP1 expression in the epithelial cell sample in the presence of the test compound relative to the absence of the test compound. In some embodiments, the epithelial cell sample is selected from the group consisting of prostate cancer cells and colon cancer cells. In some embodiments, detecting comprises detecting HIP1 mRNA. In other embodiments, detecting comprises detecting a HIP1 polypeptide. In some embodiments, the cell is in vitro. In other embodiments, the cell is in vivo. In some embodiments, the test compound comprises an antisense compound. In other embodiments, the test compound comprises a drug. In some embodiments, the drug is an antibody. In other embodiments, the drug specifically binds to HIP1.

The present invention provides the use of HIP1 as a marker to distinguish cancer cells from normal epithelial cells. The present invention further provides use of HIP1 as a marker to distinguish prostate or colon cancer cells from normal prostate or colon epithelium. The present invention additionally provides the use of an antibody that specifically binds to HIP1 to distinguish cancer cells from normal epithelial cells. The present invention also provides the use of an antibody that specifically binds to HIP1 to distinguish prostate or colon cancer cells from normal prostate or colon epithelium.

In some embodiments, the present invention provides a method of screening compounds, comprising: providing a first cell sample comprising cells expressing wild-type HIP1; a second cell sample comprising cells, wherein said cells do not express HIP1; one or more test compounds; and contacting the first and seconds samples with the test compound; and detecting a decrease in viability in the first sample relative to the second sample. In some preferred embodiments, the decrease in viability is due to programmed cell death. In some embodiments, the first and second cell samples comprise embryonic fibroblast cells. For example, in some embodiments, the first cell sample comprises embryonic fibroblast cells derived from wild-type mice and the second cell sample comprises embryonic fibroblast cells derived from HIP1 knockout mice. In other embodiments, the first and second cell samples comprise first and second human cancer cell lines. In some embodiments, the second cancer cell line comprises colo205 cells. In some embodiments, the test compound comprises a library of test compounds. In some embodiments, the test compound comprises a lipid analogue. In some embodiments, the test compound binds to HIP1. For example, in some embodiments, thetest compound binds to the ENTH domain of HIP1.

The present invention further provides a composition comprising a mutant HIP1 nucleic acid sequence lacking the ENTH domain. In some embodiments, the nucleic acid sequence comprises SEQ ID NO: 3. The present invention also provides a composition comprising a polypeptide encoded by the nucleic acid sequence.

In some embodiments, the present invention provides the HIP1 nucleic acid sequence of SEQ ID NO:1. In some embodiments, the present invention provides the polypeptide sequence of SEQ ID NO:2.

The present invention also provides a composition comprising a mutant HIP1 polypeptide that induces cell death when expressed in a cell. In some embodiments, the mutant HIP1 polypeptide is lacking a ENTH domain. In some embodiments, the HIP1 polypeptide comprises SEQ ID NO: 4. In some embodiments, the present invention provides a nucleic acid sequence encoding the polypeptide The present invention additionally provides a non-human transgenic animal lacking a functional HIP1 gene. In some embodiments, the non-human transgenic animal is a mouse. In some embodiments, the animal comprises a knock-out of the HIP1 gene. In some embodiments, the knock-out is a conditional knock-out. In other embodiments, the animal comprises a knock-in of the HIP1 gene.

In still further embodiments, the present invention provides a composition comprising a drug, wherein the drug binds to wild type HIP1 but not a HIP1 ENTH deletion mutant, and wherein the drug inhibits HIP1 biological activity. In some embodiments, the drug binds to the ENTH domain of HIP1. In some embodiments, the drug is a lipid analogue. In some embodiments, the lipid analogue is a phosphoinositide mimetic.

DESCRIPTION OF THE FIGURES

FIG. 3 shows the results of immunohistochemical analysis of colon and prostate tumors.

FIG. 4 shows the relationship of HIP1 expression with clinical outcome in prostate cancer patients.

FIG. 5 shows a table of prostate tissue microarray analysis results for 114 patients.

FIG. 6 shows HIP1 expression in a transgenic mouse model of prostate cancer (TRAMP) (FIG. 6A) and effects of functional knockout of HIP1 on cellular survival (FIG. 6B).

FIG. 7 shows the nucleic acid sequence of SEQ ID NO: 1.
FIG. 8 shows the amino acid sequence of SEQ ID NO: 2.
FIG. 9 shows the nucleic acid sequence of SEQ ID NO: 3.
FIG. 10 shows the amino acid sequence of SEQ ID NO: 4.
FIG. 15 shows the vector construction strategy for HIP1/PDGFβR knock-in.
FIG. 17 shows the nucleic acid sequence of HIP1 untranslated regions and Exons 1 and 2 (SEQ ID NO:6).

GENERAL DESCRIPTION OF THE INVENTION

Figure 1:
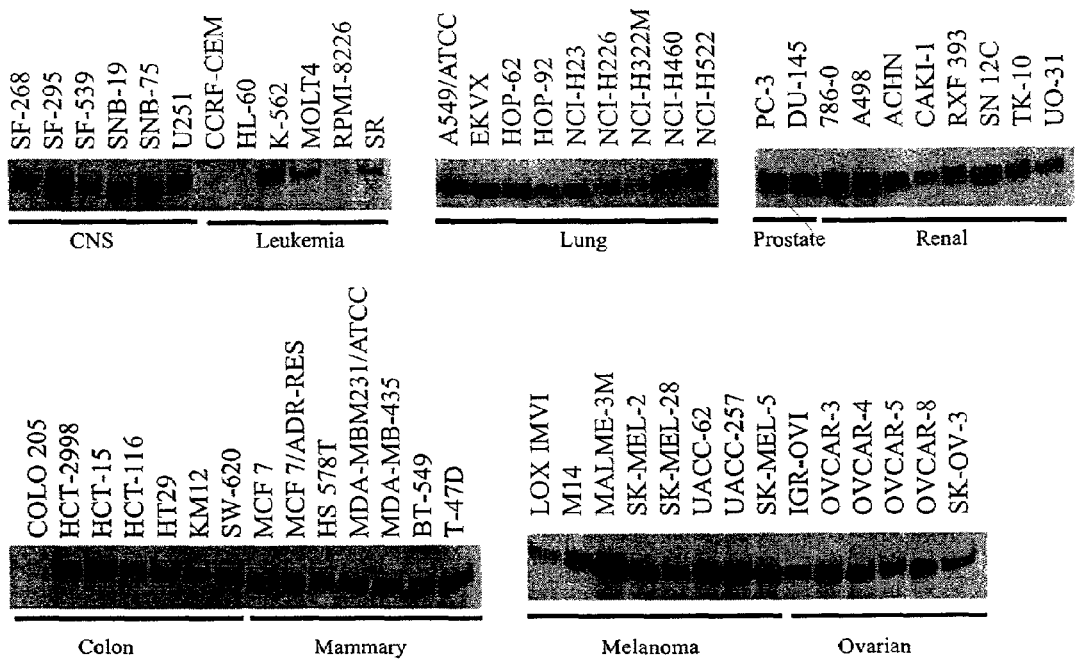
FIG. 1 shows a Western blot analysis of the NCI 60 cancer-cell line screen.

Originally identified as a protein that interacts with huntingtin (Kalchman et al., Nat.Genet. 16:44 [1997]; Wanker et al., Hum. Mol. Genet. 6:487 [1997]), HIP1 is a co-factor in clathrin mediated trafficking (Metzler et al., J. Biol. Chem. 276: 39271 [2001]; Mishra et al., JBC [2001]; Rao et al., Mol Cell Biol 21: 7796 [2001]; Waelter et al., Hum. Mol. Genet. 10: 1807 [2001]). The primary structure of HIP1 predicts an epsin N-terminal homology (ENTH) domain, a leucine zipper motif and a carboxyl terminus homologous to TALIN. ENTH domains bind to polyphosphoinositide signaling lipids and have so far only been found in co-factors of clathrin mediated trafficking (Itoh et al., Science 291:1047 [2001]; Ford et al., Science 291:1051 [2001]). Binding to lipid localizes the co-factors, including HIP1, to areas of receptor-mediated endocytosis to assist in clathrin lattice formation.

The present invention is not limited to a particular mechanism. Indeed, an understanding of the mechanism is not necessary to practice the present invention. Nonetheless, it is contemplated that HIP1 expression promotes proliferation or cell survival by reducing the growth factor dependence of cells. HIP1 over-expression may dysregulate growth factor receptor cell surface density or growth factor secretion, as a consequence of its role in clathrin-mediated trafficking.

The present invention demonstrates, using cancer cell lines, immunohistochemistry (IHC) and tissue microarrays, that HIP1 is specifically over-expressed in colon and prostate tumors but is absent in normal prostatic and colonic epithelium. The expression of HIP1 in prostate cancer specimens from multiple patients was examined and found to be expressed with an increased frequency in prostatic intraepithelial neoplasia (PIN), clinically localized prostate cancer (PCA), and metastatic PCA. Expression of HIP1 in human prostate tumors was evaluated in detail and correlated with progression of prostate cancer. This was evidenced by a lack of expression in the benign epithelium compared to the highest frequencies of expression in the most deadly cases of metastatic prostate cancer. In addition, there was a survival advantage in patients whose prostate confined prostate cancers did not express HIP1 compared to patients whose tumors did express HIP1. This independent prognostication is exemplified by the patients with HIP1 negative tumors who did well, in whom traditional pathologic indicators (stage and Gleason score) would have indicated a poor outcome. Its role in tumorigenesis was further strengthened by its overexpression in prostate cancers in a mouse model of prostate cancer and data suggesting that normal HIP1 expression maintains cell survival. The present invention is not limited to a particular mechanism. Indeed, an understanding of the mechanism is not necessary to practice the present invention. Nonetheless, it is contemplated that HIP1 participates in the progression of PCA.

In addition, it is contemplated that, similar to prostate cancer, the stratification of colonic adenocarcinomas based on HIP1 staining has predictive value both with regard to tumor aggressiveness and patient survival. Because the vast majority of colonic tumors produce a similar histologic picture it is difficult to obtain prognostic information from histologic analysis of tumor cells. Thus, the clinical outcome from a large cohort of patients with colon cancer whose tumor HIP1 status is known provides useful clinical information. Accordingly, the present invention provides a molecular marker whose expression is a valuable clinical tool for prognostication in the care of patients with two of the most common forms of cancer.

Definitions

To facilitate an understanding of the present invention, a number of terms and phrases are defined below:

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "a monoclonal antibody having substantially the same properties as antibodies secreted by a hybridoma selected from the group consisting of those deposited as ATCC numbers PTA-3901, PTA-3902 and PTA-4071" refers to a monoclonal antibody having substantially the same properties as those disclosed in Example 1 (ATCC numbers PTA-3901, PTA-3902 and PTA-4071), including but not limited to, specific binding to human and mouse HIP1 protein and "specifically binds to HIP1 with low background binding."

As used herein, the term "specifically binding to HIP1 with low background binding" refers to an antibody that binds specifically to HIP1 protein (e.g., in an immunohistochemistry assay) but not to other proteins (e.g., lack of non-specific binding).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the terms "epithelial tissue" or "epithelium" refer to the cellular covering of internal and external surfaces of the body, including the lining of vessels and other small cavities. It consists of cells joined by small amounts of cementing substances. Epithelium is classified into types on the basis of the number of layers deep and the shape of the superficial cells.

As used herein, the term "normal epithelium of prostate or colon" refers to prostate or colon epithelium that does not show any detectable indication of cancerous or pre-cancerous conditions.

As used herein, the term "cancerous epithelium of prostate or colon" refers to prostate or colon epithelium that shows a detectable indication of cancerous or pre-cancerous conditions.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass or increased PSA level) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests (e.g., PSA).

As used herein, the term "initial diagnosis" refers to a test result of initial cancer diagnosis that reveals the presence or absence of cancerous cells (e.g., using a biopsy and histology). An initial diagnosis does not include information about the stage of the cancer or the risk of prostate specific antigen failure.

As used herein, the term "prostate specific antigen failure" refers to the development of high prostate specific antigen levels in a patient following prostate cancer therapy (e.g., surgery).

As used herein, the term "risk of developing prostate specific antigen failure" refers to a subject's relative risk (e.g., the percent chance or a relative score) of developing prostate specific antigen failure following prostate cancer therapy.

As used herein, the term "prostate tumor tissue" refers to cancerous tissue of the prostate. In some embodiments, the prostate tumor tissue is "post surgical prostate tumor tissue."

As used herein, the term "post surgical tumor tissue" refers to cancerous tissue (e.g., prostate tissue) that has been removed from a subject (e.g., during surgery).

As used herein, the term "identifying the risk of said tumor metastasizing" refers to the relative risk (e.g., the percent chance or a relative score) of a tumor (e.g., prostate tumor tissue) metastasizing.

As used herein, the term "identifying the risk of said tumor recurring" refers to the relative risk (e.g., the percent chance or a relative score) of a tumor (e.g., prostate tumor tissue) recurring in the same organ as the original tumor (e.g., prostate).

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue and the stage of the cancer. Cancers may be characterized by the identification of HIP1 in tumor tissues.

As used herein, the term "characterizing tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression of HIP1.

As used herein, the term "reagent(s) capable of specifically detecting HIP1 expression" refers to reagents used to detect the expression of HIP1. Examples of suitable reagents include but are not limited to, nucleic acid probes capable of specifically hybridizing to HIP1 mRNA or cDNA, and antibodies (e.g., monoclonal antibodies of the present invention).

As used herein, the term "instructions for using said kit for detecting cancer in said subject" includes instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalency determination. Additional information is available at the Internet web page of the U.S. FDA.

As used herein, the term "non-human transgenic animal lacking a functional HIP1 gene" refers to a non-human animal (preferable a mammal, more preferably a mouse) whose endogenous HIP1 gene has been inactivated (e.g., as the result of a "HIP knockout" or a HIP1 knock-in").

As used herein, the terms "HIP1 knockout" refers to a non-human animal (e.g., a mouse) lacking a functional HIP1 gene. In some embodiments, the entire HIP1 gene is deleted. In other embodiments, the gene is inactivated via other means (e.g., deletion of essential portions or inversions of some or all of the HIP1 gene). In other embodiments, the HIP1 gene is inactivated using antisense inhibition. HIP1 knockout include conditional knockouts (e.g., selective inhibition of gene activity). HIP1 knockout mice may be made using any suitable method including, but not limited to, those described herein. HIP1 genes can also be inactivated via the construction of a "HIP1 knock-in" in which the gene is inactivated by the insertion of exogenous DNA into a region of the gene required for function.

As used herein, the term "ENTH domain of HIP1" refers to the epsin N-terminal homology domain of HIP1. In some embodiments, the ENTH domain comprises amino acids 1-187 of SEQ ID NO: 2. The ENTH domain is believed to be responsible for HIP1 binding to polyphosphoinositol lipids, which are involved in signaling. As used herein, the term "HIP1 ENTH deletion mutant" refers to a HIP1 polypeptide that lacks the ability to bind to polyphosphoinositol lipids (e.g., because of complete or partial deletion or mutation of the ENTH domain). In preferred embodiments, expression of "HIP1 ENTH deletion mutants" results in cell death. One example of a "HIP1 ENTH deletion mutant" is the polypeptide described by SEQ ID NO: 4.

As used herein, the term "lipid analogue" refers to a small molecule that has one or more structural features (e.g., a hydrophobic domain) of a lipid (e.g., fatty acids). Lipid analogues includes modified lipids, whether synthetic or naturally occurring.

As used herein, the term "mimetic" refers to a small molecule compound that mimics the binding of a ligand (e.g., polyphosphoinositol lipid) to HIP1. A mimetic that mimics the binding of a polyphosphoinositol lipid is referred to as a "polyphosphoinositol mimetic." In some embodiments, mimetics are lipid analogues. Preferred mimetics bind to the ENTH domain of HIP1 and inhibit polyphosphoinositol lipid signaling. Particularly preferred mimetics induce cell death in cancer cells expressing HIP1 but not normal cells.

As used herein, the term "detecting a decrease in viability" refers to a decrease in the number of living cells in a culture. In preferred embodiments, the decrease is due to the induction of programmed cell death (e.g., apoptosis) in some or all of the cells in a population.

As used herein, the term "induces cell death" refers to a molecule (e.g., a test compound or a drug) that induces a programmed cell death (e.g., apoptosis).

As used herein, the term "drug that inhibits HIP1 biological activity" refers to a drug that inhibits one or more biological activities of HIP1 (e.g., ligand binding and signaling). Preferred drugs are those that inhibit polyphosphoinositol lipid binding and subsequent signaling.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4·H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4·H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4·H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acids will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, N.Y., pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk$^-$ cell lines, the CAD gene that is used in conjunction with CAD-deficient cells and the mammalian hypoxanthine-guanine phosphoribosyl transferase (hprt) gene that is used in conjunction with hprt$^-$ cell lines. A review of the use of selectable markers in mammalian cell lines is provided in Sambrook, J. et al., Molecular Cloning: A Laboratory Manual, 2nd ed., Cold Spring Harbor Laboratory Press, N.Y. (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention provides novel antibodies to HIP1. The present invention further provides methods for providing cancer (e.g., colon and prostate cancers) diagnoses, prognoses, and treatments (e.g., using the monoclonal antibodies of the present invention). The present invention further provides methods of screening potential therapeutic compounds for HIP1 inhibitory properties.

I. HIP1 as a Marker for Cancer

The present invention relates to compositions and methods for cancer diagnostics, including but not limited to, HIP1 cancer markers. In particular, the present invention provides markers (e.g., HIP1) whose expression is specifically altered in cancerous tissues (e.g., epithelial tissues such as prostate and colon). Such markers find use in the diagnosis and characterization of cancer.

A. Identification of Markers

Experiments conducted during the development of the present invention resulted in the generation of highly specific and sensitive monoclonal antibodies against Huntingtin Interacting Protein 1 (HIP1). Three of the anti-HIP1 antibodies were used to investigate the presence of HIP1 in cancer tissues. HIP1 was found to be strongly expressed in a majority of prostate cancer and colon cancer specimens, but rarely and weakly expressed in normal prostate and colon tissue. Accordingly, the present invention provides methods for diagnosing cancers (e.g., prostate and colon cancers) by detecting the presence of HIP1. In addition, increased HIP1 expression was found to correlate with a negative prognosis.

B. HIP1 Mutants

Figure 11:
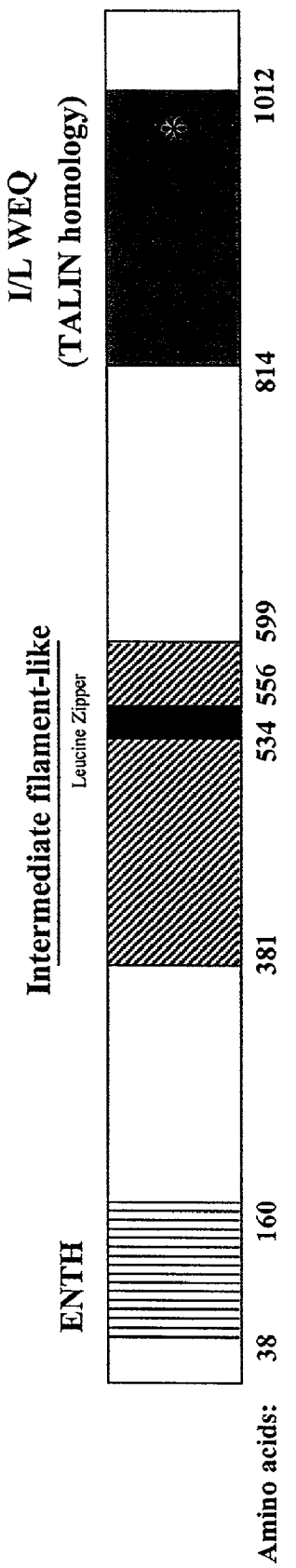
FIG. 11 shows the domain structure of HIP1.

The present invention further provides HIP1 mutants. Most HIP1 mutants can be expressed in combination with endogenous HIP1 without seriously affecting cell survival or proliferation. However, a construct identified during the development of the present invention caused cells to undergo cell death upon expression. The mutant lacked the ENTH domain of HIP1 (See FIG. 11 for a description of the domain structure of HIP1). The HIP1 ENTH deletion mutant generated during the development of the present invention is described in Example 3 and SEQ ID NOs: 3 and 4. The ENTH domain is responsible for HIP1 binding to polyphosphoinositol lipids, which act as signaling molecules. The present invention is not limited to a particular mechanism. Indeed, an understanding of the mechanism is not necessary to practice the present invention. Nonetheless, it is contemplated that the ENTH deletion mutants disrupt HIP1's normal role of linking clathrin mediated trafficking to signaling. In addition, over-expression of wild-type HIP1 prevented the induction of cell death by the ENTH deletion mutant. The present invention is not limited to a particular mechanism. Indeed, an understanding of the mechanism is not necessary to practice the present invention.

Figure 14:
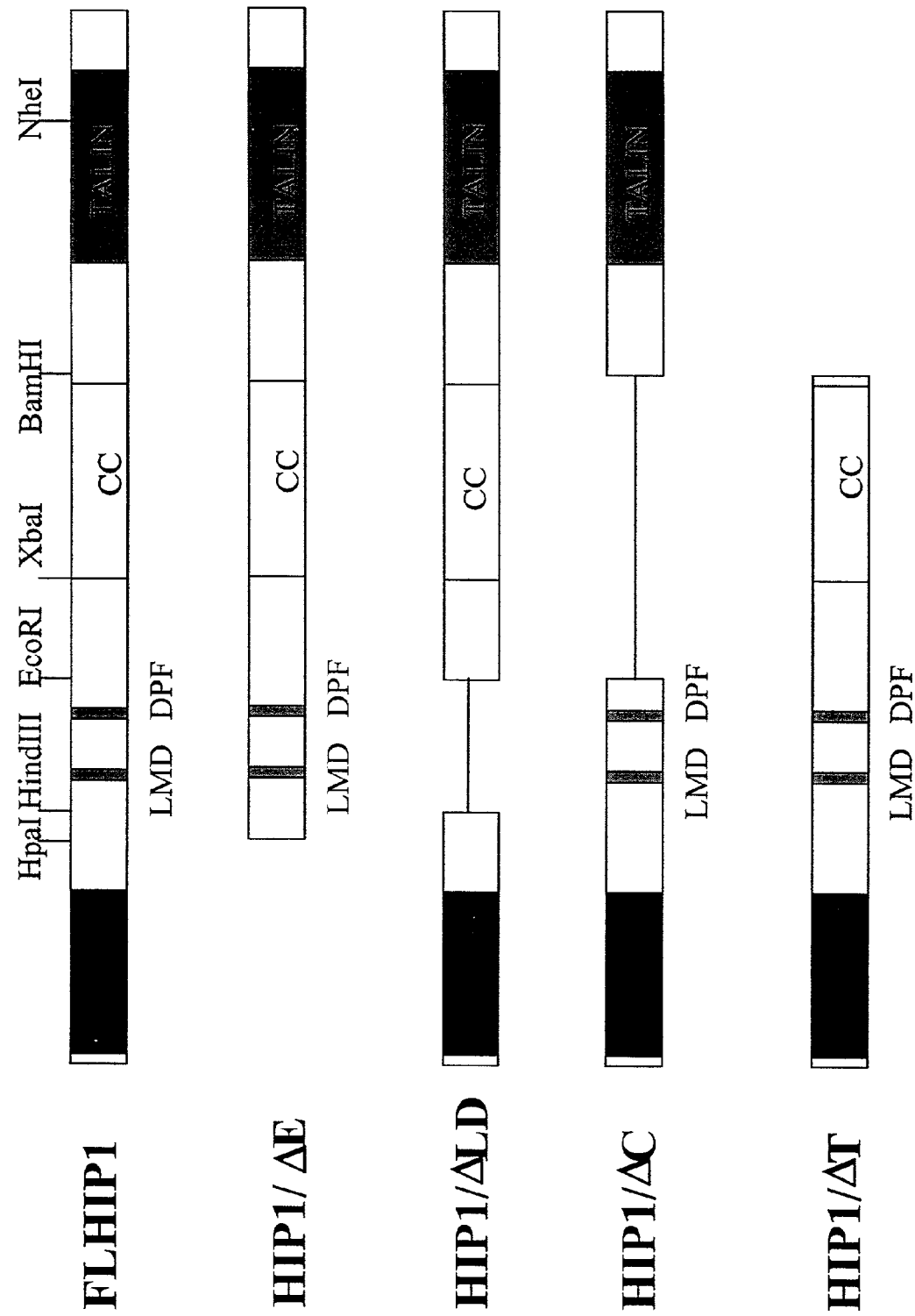
FIG. 14 shows some HIP1 mutants of some embodiments of the present invention.

The present invention is not limited to the ENTH deletion mutant of SEQ ID NOs: 3 and 4. The present invention contemplates any mutation that alters or inhibits the normal biological function of HIP1. In some embodiments, the HIP1 mutant is one of the mutants described in FIG. 14. In some preferred embodiments, the mutation results in the inactivation of the ENTH domain (e.g., as determined by the ability of the mutant to induce cell death when expressed). Preferred ENTH deletion mutants are induce cell death when expressed alone but the induction of cell death is prevented by over-expression of a wild-type HIP1. HIP1 mutants can be generated using any suitable method including, but not limited to, standard molecular biology techniques well known in the art or by isolation of naturally occurring mutants.

C. Detection of HIP1

In some embodiments, the present invention provides methods for detection of HIP1. In preferred embodiments, the presence of HIP1 protein or mRNA is measured directly. In some embodiments, HIP1 mRNA or protein is detected in tissue samples (e.g., biopsy samples). In other embodiments, HIP1 mRNA or protein is detected in bodily fluids (e.g., serum, plasma, or urine). The present invention further provides kits for the detection of HIP1. In preferred embodiments, the presence of HIP1 is used to provide a diagnosis or prognosis to a subject.

In some preferred embodiments, HIP1 protein is detected. Protein expression may be detected by any suitable method. In some embodiments, proteins are detected by binding of an antibody specific for the protein. In some preferred embodiments, the monoclonal antibody described in Example 1 below is utilized. The present invention is not limited to a particular antibody. Any antibody (monoclonal or polyclonal) that specifically detects HIP1 may by utilized. Methods for the generation of antibodies are described below.

Antibody binding is detected by techniques known in the art. For example, in some embodiments where HIP1 protein is detected in bodily fluids, antibody binding is detected using a suitable technique, including but not limited to, radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays. In other embodiments, where HIP1 protein is detected in tissue samples, immunohistochemistry is utilized for the detection of antibody binding.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include, but are not limited to, those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a diagnosis and/or prognosis based on the presence or absence of a series of proteins corresponding to cancer markers is utilized.

In other embodiments, the immunoassay described in U.S. Pat. Nos. 5,599,677 and 5,672,480, each of which is herein incorporated by reference, is utilized. In other embodiments, proteins are detected by immunohistochemistry.

In other embodiments, HIP1 is detected at the level of HIP1 RNA. In some embodiments, HIP1 RNA is detected by measuring the expression of corresponding mRNA in a tissue sample (e.g., prostate or colon tissue). mRNA expression may be measured by any suitable method, including but not limited to, those disclosed below.

In some embodiments, RNA is detected by Northern blot analysis. Northern blot analysis involves the separation of RNA and hybridization of a complementary labeled probe. Methods for Northern blot analysis are well known in the art.

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to a oligonucleotide probe. A variety of hybridization assays using a variety of technologies for hybridization and detection are available. For example, in some embodiments, TaqMan assay (Applied Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

D. Kits

In some embodiments, the present invention provides kits for the detection and characterization of cancer (e.g., prostate and colon cancer). In some embodiments, the kits contain antibodies specific for HIP1, in addition to detection reagents and buffers. In other embodiments, the kits contain reagents specific for the detection of HIP1 mRNA or cDNA (e.g., oligonucleotide probes or primers). In preferred embodiments, the kits contain all of the components necessary to perform a detection assay, including all controls, directions for performing assays, and any necessary software for analysis and presentation of results.

II. Antibodies

The present invention provides isolated antibodies. In preferred embodiments, the present invention provides monoclonal antibodies that specifically bind to an isolated polypeptide comprised of at least five amino acid residues of HIP1. These antibodies find use in the diagnostic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against HIP1). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against HIP1) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, HIP1 protein (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

In some embodiments, antibodies (e.g., monoclonal antibodies) are humanized. Such humanized antibodies find particular use in the cancer immunotherapies described below. Humanized antibodies are altered in order to make them less immunogenic to humans, e.g., by constructing chimeric antibodies in which a mouse antigen-binding variable domain is coupled to a human constant domain. Humanized antibodies are typically human antibodies in which some CDR residues and possibly some FR residues are substituted by residues from analogous sites in rodent antibodies. Methods for humanizing antibodies are well known in the art and include but are not limited to, those disclosed in U.S. Pat. Nos. 6,054, 297, 4,816,567, 6,180,377, 5,871,907, 5,585,089, and 6,180, 370, each of which is herein incorporated by reference.

III. Drug Screening

In some embodiments, the present invention provides drug screening assays (e.g., to screen for anticancer drugs). The screening methods of the present invention utilize HIP1. For example, in some embodiments, the present invention provides methods of screening for compounds that alter (e.g., increase or decrease) the expression of HIP1. In some embodiments, candidate compounds are antisense agents (e.g., oligonucleotides) directed against HIP1. See Section IV below for a discussion of antisense therapy. In other embodiments, candidate compounds are antibodies (e.g., those described in Section II above and the below Example. In other embodiments, candidate compounds are small molecules. In some embodiments, given the fact that the ENTH deletion HIP1 construct has the phosphoinositide binding site of HIP1 deleted, lipid analogues are utilized as candidate compounds. In other embodiments, non-lipid analogue small molecules are utilized as candidate compounds.

A. HIP1 Expression Assays

In one screening method, candidate compounds are evaluated for their ability to alter HIP1 expression by contacting a compound with a cell expressing HIP1 and then assaying for the effect of the candidate compounds on expression. In some embodiments, the effect of candidate compounds on expression of HIP1 is assayed for by detecting the level of cancer marker mRNA expressed by the cell. mRNA expression can be detected by any suitable method, including but not limited to, those disclosed herein.

In other embodiments, the effect of candidate compounds is assayed by measuring the level of HIP1 expression. The level of polypeptide expressed can be measured using any suitable method, including but not limited to, those disclosed herein.

B. Cellular Assays

In some preferred embodiments, the present invention provides methods of identifying small molecule inhibitors of HIP1. In some embodiments, methods are utilized that identify compounds that mimic the effect of the ENTH deletion mutant described in Example 3 (e.g., cause cell death). For example, in some embodiments, a high throughput screening method comprising the use of HIP1+embryonic fibroblasts obtained from wild-type mice and HIP1−/−embryonic fibroblasts obtained from HIP1 knockout mice is utilized (See e.g., Example 5). These fibroblasts are cultured and libraries of therapeutic compounds are added to the cultures. Specific inhibitors of HIP1 are then identified as compounds that kill the HIP1+fibroblasts but not the HIP1−fibroblasts.

In other embodiments, a screen against human HIP1 is performed by using HIP1 expressing cancer cell lines (e.g., the majority of cancer cell lines) and HIP1 non-expressing human cancer cell lines (e.g., colo205 cell lines, ATCC; (See e.g., Example 5)). Such cell lines are cultured in the presence of a library of therapeutic compounds to identify compounds that kill HIP1+ but not HIP1−cell lines. These methods represent effective ways of screening for therapeutic compounds against a variety of epithelial cancers.

C. In Vitro Assays

In some embodiments, In vitro drug screens are performed using purified wild type HIP1 and the HIP1 ENTH deletion mutant described in Example 3. In some embodiments, the HIP1 proteins are immobilized to facilitate separation of complexed from uncomplexed forms of one or both of the proteins, as well as to accommodate automation of the assay. Binding of a test compound to HIP1 or HIP1 ENTH deletion mutant can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/AIP-6 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and the non-adsorbed protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of protein binding or activity determined using standard techniques.

Other techniques for immobilizing proteins on matrices can also be used in the screening assays of the invention. For example, HIP1 or HIP1 ENTH deletion mutant can be immobilized utilizing conjugation of biotin and streptavidin. Biotinylated HIP1 or HIP1 ENTH deletion can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with HIP1 or HIP1 ENTH deletion mutants but which do not interfere with binding of the protein to test compounds can be derivatized to the wells of the plate, and unbound protein trapped in the wells by antibody conjugation. Methods for detecting such complexes, in addition to those described above for the GST-immobilized complexes, include immunodetection of complexes using antibodies reactive with HIP1 or HIP1 ENTH deletion mutants, as well as enzyme-linked assays that rely on detecting an enzymatic activity associated with the HIP1 or HIP1 ENTH deletion mutant.

In other embodiments, a competitive drug screening assays in which neutralizing antibodies capable of binding wt HIP1 specifically compete with a test compound for binding HIP1 are utilized. In this manner, the antibodies can be used to detect the presence of any compound that shares one or more antigenic determinants with HIP1.

D. In vivo Assays

In still further embodiments, transgenic animals having altered (e.g., inactivated or overexpressed) HIP1 gene are utilized in drug screening applications. Exemplary transgenic animals are described below and in Example 4. For example, in some embodiments, compounds are screened for their ability to reduce tumors in wild type mice but not HIP1 deletion mutants. In some preferred embodiments, HIP1 conditional knock-out mice are utilized in such an assay. In some embodiments, the conditional HIP1 mutants described in Example 4 are utilized. These mice have a functional HIP1 gene that can be inactivated via the administration of an adenoviral vector containing the cre gene.

In other embodiments, transgenic animals that overexpress HIP1 in tissues that typically have HIP1+tumors (e.g., breast, prostate, and colon) are utilized for drug screening. Such mice are administered libraries of compounds and a decrease in tumor size or lack of expression of HIP1 is screened for.

In still further embodiments, the mouse model of prostate cancer described in Example 2 is utilized in drug screening applications. Such mice are administered libraries of compounds and a decrease in tumor size is screened for.

IV. Cancer Therapies

In some embodiments, the present invention provides therapies for cancer (e.g., prostate and colon cancer). In some embodiments, therapies target HIP1.

A. Antisense Therapies

In some embodiments, the present invention targets the expression of HIP1. For example, in some embodiments, the present invention employs compositions comprising oligomeric antisense compounds, particularly oligonucleotides (e.g., those identified in the drug screening methods described above), for use in modulating the function of nucleic acid molecules encoding HIP1, ultimately modulating the amount of HIP1 expressed. This is accomplished by providing antisense compounds that specifically hybridize with one or more nucleic acids encoding HIP1. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of HIP1. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding HIP1. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference.

Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$OCH$_3$, O($CH_2$)$_n$NH$_2$, O($CH_2$)$_n$CH$_3$, O($CH_2$)$_n$ONH$_2$, and O($CH_2$)$_n$ON[($CH_2$)$_n$CH$_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O(CH$_2$)$_2$ON(CH$_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

Other preferred modifications include 2'-methoxy(2'-O—CH$_3$), 2'-aminopropoxy(2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Genetic Therapies

The present invention contemplates the use of any genetic manipulation for use in modulating the expression of HIP1. Examples of genetic manipulation include, but are not limited to, gene knockout (e.g., removing the HIP1 from the chromosome using, for example, recombination), expression of antisense constructs with or without inducible promoters, and the like. In other embodiments, genetic manipulation is used to deliver the HIP1 ENTH deletion mutants (e.g., to cancer cells). Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. patent application Ser. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target HIP1 expressing tumors. In preferred embodiments, the antibodies used for cancer therapy are humanized antibodies.

In some embodiments, the therapeutic antibodies comprise an antibody generated against HIP1, wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted HIP1. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Small Molecule Drugs

In some embodiments, the present invention provides drugs (e.g., small molecule drugs) that reduce or eliminate cancer by inhibiting the biological activity of HIP1. In some embodiments, small molecule drugs are identified using the drug screening methods described above. In some embodiments, the small molecule drugs are lipid analogues. In some preferred embodiments, the small molecule drugs mimic the cell death inducing effect of the ENTH deletion mutant of HIP1. In particularly preferred embodiments, the small molecule drugs of the present invention result in the cell death of cancer, but not normal cells. In some embodiments, small molecule drugs are identified using the drug screens described herein (e.g., in Example 5 and Section III above).

E. Pharmaceutical Compositions

The present invention further provides pharmaceutical compositions (e.g., comprising the therapeutic compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

V. Transgenic Animals Expressing HIP1

The present invention contemplates the generation of transgenic animals comprising an exogenous HIP1 gene or mutants and variants thereof (e.g., truncations, deletions, insertions, or single nucleotide polymorphisms). In other embodiments, the present invention provides transgenic animals with a knock-out of the HIP1 gene. In still further embodiments, transgenic animals overexpress HIP1 in specific tissues (e.g., breast, colon, and prostate). In preferred embodiments, the transgenic animal displays an altered phenotype (e.g., increased or decreased presence of HIP1) as compared to wild-type animals. Exemplary transgenic animals are described in Example 4. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the microinjection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al, EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

Example 1

HIP1 Expression in Cancerous and Non-Cancerous Tissues

A. Monoclonal Antibodies

The antibodies to HIP1 were generated by isolating a human HIP1 cDNA and creating a bacterial expression vector containing the sequences encoding the carboxyl half of the HIP1 protein. The expressed and purified recombinant protein was use to immunize mice and create monoclonal antibodies by standard methods. The specificity of the antibodies to HIP1 was confirmed by comparing Western blot analyses of murine embryonic fibroblast extracts derived from embryos with HIP1 deleted and their wild type litter mates (data not shown). Three monoclonal antibodies were found to be useful for Western blot analysis of HIP1, as well as for IHC of human tissue. These antibodies were designated HIP1-4B10, HIP1-1A1 and HIP1-1B11. Antibodies 4B10 and 1A1 recognize only human HIP1. Antibody 1B11 recognizes both human and mouse HIP1. The hybridomas producing antibodies HIP1-4B10, 1A1, HIP1-1B11 and HIP1-1A1 were deposited with ATCC under numbers PTA-3901 (HIP1-1B11), PTA-3902 (HIP1-4B10) and PTA-4071 (HIP1 -1A1).

B. Tissue Microarrays

A high-density tissue microarray of multiple primary tumors was obtained from the National Cancer Institute. High-density tissue mircroarrays for prostate tumors were assembled as previously described (Perrone et al., J. Natl. Cancer Inst., 92:937 [2000]). Cases of clinically localized prostate cancer were from the University of Michigan Prostate SPORE tumor bank. The advanced prostate tumors were collected from a series of rapid autopsies performed at the University of Michigan on men who died of metastatic prostate cancer. Autopsies were performed 4-6 h after death.

C. Immunohistochemistry

Standard biotin-avidin-complex IHC was performed. Immunostaining intensity was scored as absent, weak, moderate or high. In order to qualify as high, staining intensity had to be equivalent to that observed in endothelia of small blood vessels of the tissue. There was no staining when secondary antibody was used alone as a negative control.

D. Results

1. HIP1 in Cancer Cell Lines

Western blotting of extracts from the 60 cancer cell lines of the NCI's in vitro anti-cancer drug screen (Monks et al., J. Natl. Cancer inst., 83:757 [1991]) was used to investigate the expression of HIP1 in various cancers. Protein extracts (50 μg) derived from the 60 cell lines were separated on a 6% polyacrylamide gel, transferred to nitrocellulose, and blotted with a mix of the anti-HIP1 monoclonal antibodies 4B10 and 1B11.

The results demonstrated that HIP1 was highly expressed in most of the cancer cell lines (50/53) derived from solid tumors (FIG. 1). The cancers represented include colon, breast, melanoma, ovary, prostate, kidney and lung. HIP1 was expressed at low levels or was absent in cell lines derived from hematologic malignancies. The exception was the high level of HIP1 expression in the K562 cell line, which is derived from a patient with chronic myelogenous leukemia. This leukemia, when in the chronic phase, is a myeloproliferative syndrome similar to the CMML that can be caused by expression of the HIP1/PDGFβR tyrosine kinase (Ross et al., Blood 91:4419 [1998]).

Figure 2:
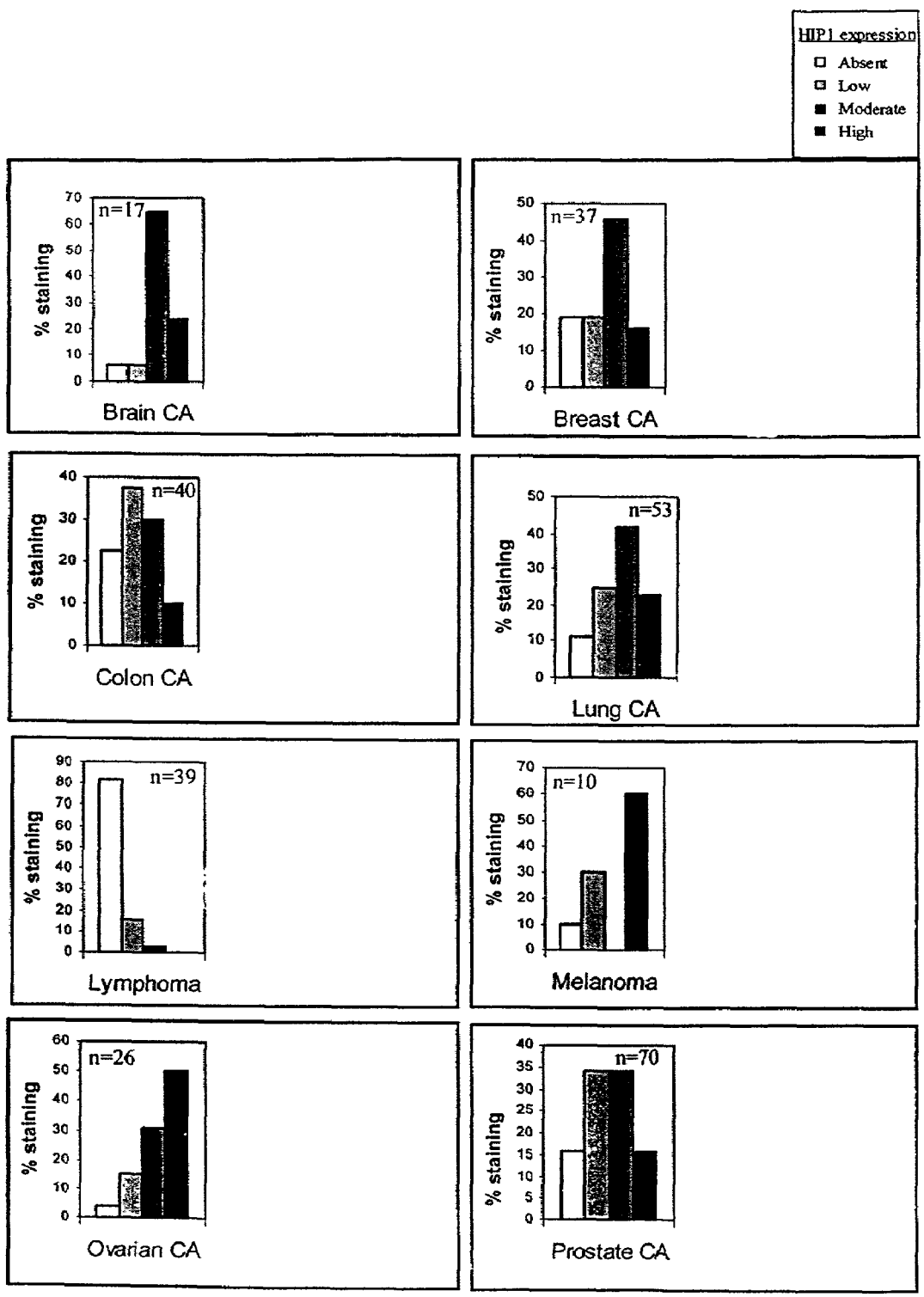
FIG. 2 shows the results of immunohistochemical analysis of the multi-tumor tissue microarray TARPI.

In order to further investigate the differential expression of HIP1, tissue microarrays were used to examine HIP1 expression in large numbers of primary tumor specimens. Microarray slides were subjected to immunohistochemical analysis with the anti-HIP1 monoclonal antibody 4B10. Using the multi-tumor tissue microarray from the National Cancer Institute designated TARP1 (Perrone et al., J. Natl. Cancer Inst., 92:937 [2000]), HIP1 was found to be moderately-to-highly expressed in a large percentage of CNS, breast, colon, lung, melanoma, ovarian and prostate cancers (FIG. 2). The highest levels of expression were found in ovarian cancer and melanoma. As predicted from the lack of expression of HIP1 in the hematologically derived NCI-ACDS cancer cell lines, there was no detectable HIP1 expression in over 80% of primary lymphoma samples.

2. HIP1 Expression in Normal Tissues

Next, IHC for HIP1 expression was examined in multiple normal tissues. HIP1 was expressed most highly in the endothelium of small blood vessels. HIP1 was also highly expressed in several secretory epithelia, including breast ductal epithelium, gastric epithelium and kidney distal tubular epithelium. Other tissues that expressed HIP1 at high levels included the lung epithelia, heart muscle, choroid plexus of the brain, various peripheral nervous system ganglia and liver. HIP1 is also expressed in the post-meiotic spermatids of the seminiferous tubules of the testis. The epithelium of the colon and prostate did not detectably express HIP1.

3. HIP1 Expression in Colon and Prostate Tissues

To study the expression of HIP1 in tumors where its expression seemed to be limited to the neoplastic epithelium, anti-HIP1 monoclonal antibodies were first used to stain colon cancers. Standard slides from archival tissue samples were obtained from 25 patients with well-differentiated colon cancers. In separate experiments, slides were stained with the monoclonal anti-HIP1 antibodies 4B10 and 1B11.

FIG. 3a shows a histogram of HIP1 expression in normal tissue and well differentiated colon cancer tissue. On staining with either of the anti-HIP1 antibodies (4B10 or 1B11), benign tissue was found to not express HIP1, while adjacent colon tumors had high levels of HIP1 expression. Quantitatively, benign epithelium of the colon never had moderate or high expression, whereas 48% of the well differentiated colon tumors had moderate or high HIP1 expression (FIG. 3a). 84% of benign colon epithelium samples did not express HIP1 compared to 8% of the colon tumor samples.

In addition to colon cancer, prostate cancer demonstrated moderate to high levels of HIP1 expression (FIG. 2), while benign epithelia did not express HIP1. To study the aberrant HIP1 expression in more detail, three prostate tissue microarrays containing a total of 853 tissue spots from 114 patients with localized prostate cancer were stained with the HIP1 monoclonal antibodies. These samples included benign prostate tissue, prostatic intraepithelial neoplasia (PIN) and prostate cancer (PCa). In addition, a separate tissue microarray that contained 135 tumor samples from 14 patients with hormone-refractory metastatic PCa was examined for HIP1 expression. As in the colon, striking differences were noted in staining between neoplastic and benign epithelia. PCA from the prostate tissue microarray demonstrated high HIP1 expression juxtaposed to non-HIP1 expressing benign prostatic epithelium. 95% of normal epithelium samples did not express HIP1. The remaining 5% had weak levels of expression and there was no moderate or high expression in any of the normal epithelia examined. Among neoplastic lesions, the precursor of prostate cancer, PIN, had the lowest number of samples with moderate or strong levels of HIP1 expression (25% of the 230 samples). Localized PCa had an intermediate number (51% of the 463 samples) and metastatic prostate cancer had the highest number of samples expressing moderate to strong levels of HIP1 (70% of the 135 samples). This difference in levels of HIP1 in progressively more advanced PCA was statistically significant (FIG. 3b, Pearson's chi-squared, P<0.0001).

4. Effect of HIP1 Expression on Clinical Outcome in PCA

The above experiments demonstrated that there were significant numbers of samples of colon cancer, PIN and PCA that did not express HIP1, similar to normal epithelia, which lacks HIP1 expression. The present invention is not limited to a particular mechanism. Indeed, an understanding of the mechanism is not necessary to practice the present invention. Nonetheless, since incrementally more malignant cancers had higher frequencies of HIP1 expression, it is hypothesized that different levels of HIP1 expression predict different behaviors in tumors. One way to look at these behaviors is to examine clinical outcomes.

Because PCA is a histologically heterogeneous tumor, an algorithm was devised for relating levels of HIP1 expression in multiple tumor specimens from each patient to an overall score for each patient. Because of heterogeneity of PCA and to evaluate the samples in the least biased way possible the following algorithm was developed. Heterogeneity was reflected in the PCA microarrays by the fact that each patient with PCa had multiple microarray samples (average of 4 per patient) that did not display the same levels of HIP1 staining (FIG. 4). The highest level of HIP1 expression from multiple tumor specimens was therefore used to represent the overall patient score. Next, a dichotomous relationship was defined, where each patient received either a "zero" or a "one" for absent expression versus weak, moderate or high expression, respectively. Any cases where there was only a single specimen available were excluded from analysis.

A tissue microarray that was derived from prostatic tumors surgically resected from 121 patients, as well as a tissue microarray that was derived from hormone-refractory metastatic PCa from 15 patients were used. FIG. 4a shows an analysis of HIP1 expression in individual patients reveals that there were progressively higher frequencies of HIP1 expression in benign (n=89), PIN (n=89), PCa (n=114), and metastatic cases (n=14). Conversely, there were progressively lower frequencies of the lack of HIP1 expression among the same. These differences are statistically significant (Pearson's chi-square 2; p<0.001), and the presence of HIP1 expression correlated significantly with the ordinal categories of benign vs. PIN vs. PCa vs. Metastatic (Spearman's correlation coefficient, 0.664, p<0.001).

An outcomes analysis was next performed on 463 samples of localized PCA from 114 patients represented by the third bar of each group of patients in FIG. 4a. To avoid introduction of bias, the microarrays were scored for HIP1 expression before clinical data was revealed to the readers of the microarrays. Taking the highest score of all the samples from each patient, Pearson's chi-square was used to determine if there were clinical implications associated with HIP1 expression. Various clinical parameters such as Gleason score, tumor size, seminal vesicle invasion, extra-prostatic extension, and relapse from PCa were evaluated. Men who have elevated PSA levels subsequent to radical prostatectomy die because of recurrent prostate cancer. This is termed PSA recurrence. Patients whose tumors did not stain for HIP1 expression did not develop a PSA recurrence (Table 1). In comparison a preoperative PSA of <4 (normal) compared to PSA>4 was also a significant good prognostic factor (Pearson's chi-squared; P<0.034). The ability of a HIP1 negative tumor to predict recurrence free survival, also termed negative predictive value was 100% while PSA<4 was 95.6% predictive. Table 2 demonstrates that HIP1 expression is independent of traditional histopathologic indicators as a molecular predictor of relapse from prostate cancer The survival advantage of PCa patients with tumors that had no HIP1 expression was demonstrated by the Kaplan-Meier survival curve shown in FIG. 4b. The curve compares patients with prostate confined tumors that did not express HIP1 (open circles) with those patients whose tumors did express HIP1 (open triangles). Again, the same group of 114 patients with prostate confined tumors was used in this analysis as in Table 1. All the patients that lacked HIP1 expression survived 67 months without evidence of recurrence. In contrast, 28% of the patients whose tumors expressed HIP1 died of prostate cancer. These data, together with the correlation of HIP1 expression with both metastatic tumors and overall death from prostate cancer suggest that HIP1 predicts both invasiveness as well as metastatic potential of prostate cancer.

In summary, this example describes the ability of HIP1 expression to mark colon and prostate tumors. The level of expression of HIP1 in prostate tumors was evaluated in detail and correlated with progression of prostate cancer. This was evidenced by a lack of expression in the benign epithelium compared to the highest levels of expression in the most deadly cases of metastatic PCa. In addition, there was a survival advantage in patients whose prostate confined PCA's did not express HIP1 compared to patients whose tumors did express HIP1.

TABLE 1

HIP1 expression and preoperative PSA as predictors of PSA recurrence

| Significance | No PSA recur (n, %) | PSA recur (n, %) | Pearson's $X^2$ | Two-sided p |
|---|---|---|---|---|
| HIP1 Absent | 14 (100%) | 0 (0%) | 4.034 | 0.045 |
| HIP1 Expressed | 77 (77%) | 23 (23%) | | |
| Preoperative PSA <4 | 22 (95.7%) | 1 (4.3%) | 4.482 | 0.034 |
| Preoperative PSA >4 | 69 (75.8%) | 22 (24.1%) | | |

TABLE 2

HIP1 expression is independent of traditional histopathologic indicators as a molecular predictor of relapse from prostate cancer

| | | Tumor HIP1 Staining | | |
|---|---|---|---|---|
| | | Negative (no. of patients) | Positive (no. of patients) | Significance[1] (two-tailed p) |
| Gleason Score[2] | <7 | 9 | 35 | 0.038 |
| | >7 | 5 | 65 | |
| Local Spread[3] | No | 13 | 70 | 0.044 |
| | Yes | 1 | 30 | |
| PSA recurrence[4] | No | 14 | 77 | 0.009 |
| | Yes | 0 | 23 | |

[1]Significance was calculated based on likelihood ratios, with two dichotomous categories in a two-by-two contingency table.
[2]The Gleason score is a validated pathologic measure.
[3]Local spread was defined as either extra-prostatic extension (outside the capsule of the organ) or invasion of the seminal vesicles, an adjacent organ, at the time of surgery.
[4]PSA recurrence is a surrogate for survival and is defined as an elevated PSA after radical prostatectomy.

Example 2

HIP1 Expression in a Mouse Model of Prostate Cancer

This example describes an investigation of the expression of HIP1 in a transgeric mouse model of prostate cancer, designated the TRAMP mouse (Greenberg et al., PNAS 92:3439 [1995]). The TRAMP mouse was created by use of a transgene where the rat probasin promoter drives expression of SV40 early genes (T and t; Tag). SV40 Tag interacts with p53 and the retinoblasoma gene product Rb abrogating their tumor suppressor gene functions.

HIP1 was found to be overexpressed in 50% of prostate tumors from TRAMP mice (n=10) compared to the normal prostate (FIG. 6a), suggesting that its expression is an active component of tumorigenesis in these mice. The heterogeneity of HIP1 expression is similar to that seen in human prostate cancers.

Example 3

HIP1 ENTH Mutant

Figure 12:
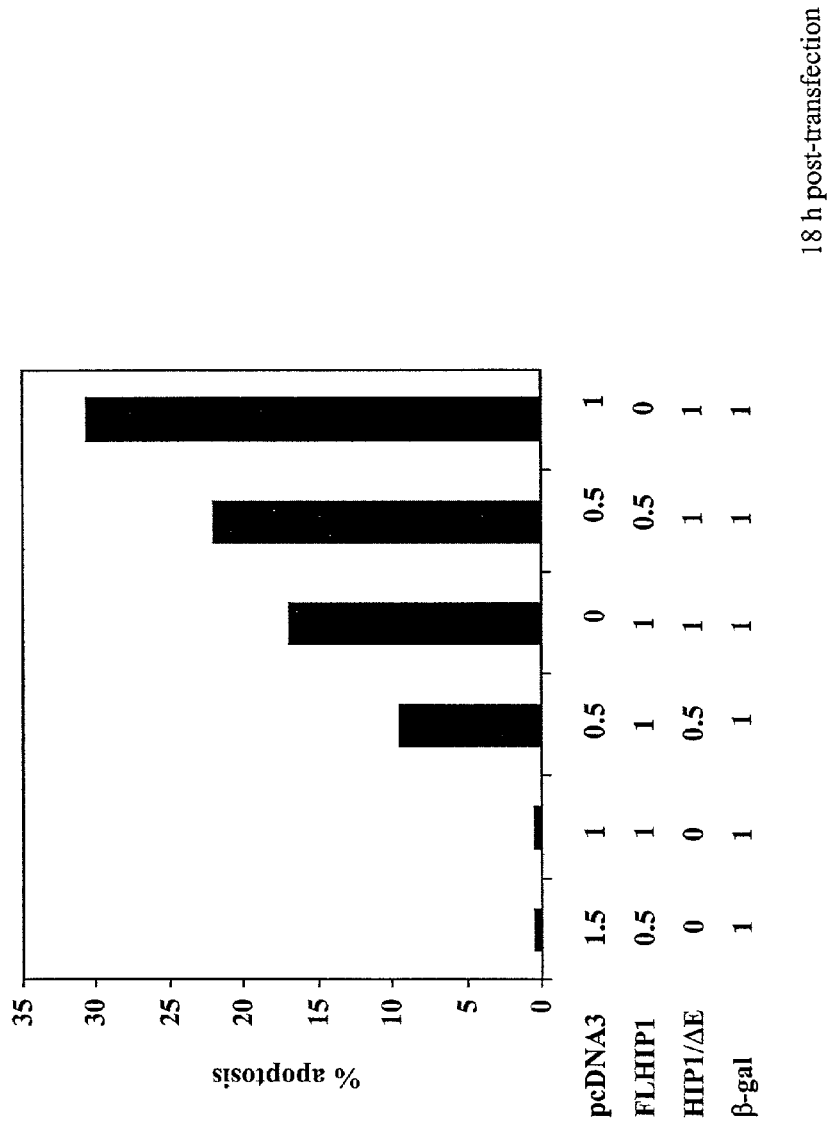
FIG. 12 shows a graph of the rescue of apoptosis caused by HIP1 ENTH deletion mutant with FLHIP1.
Figure 13:
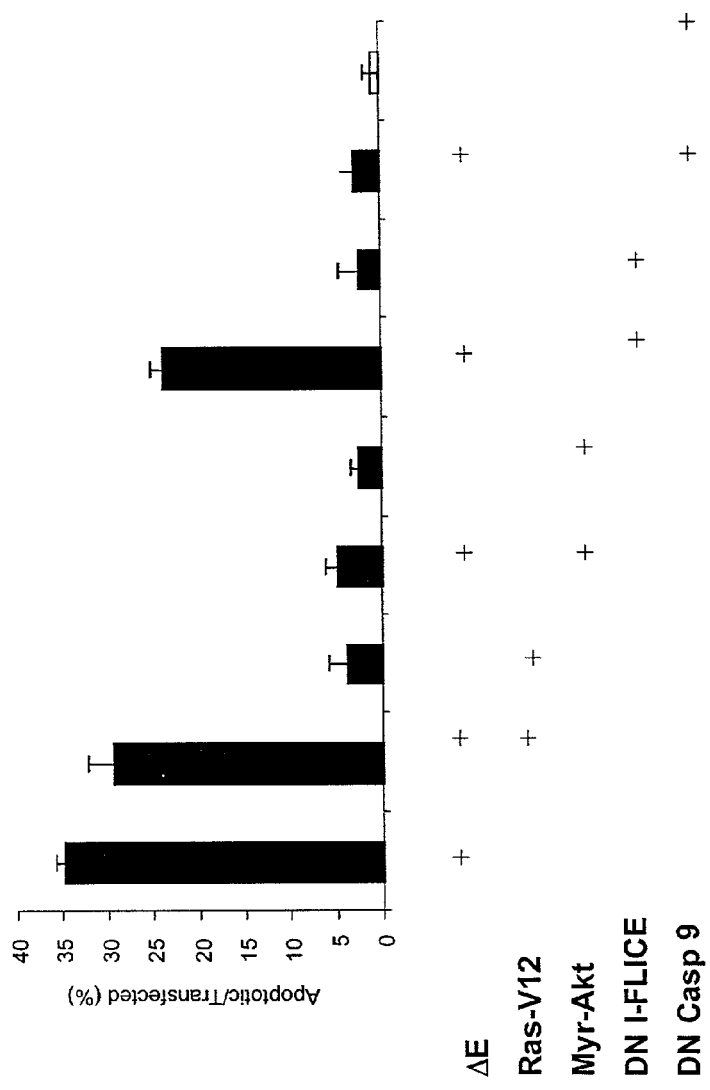
FIG. 13 shows a graph of the rescue of apoptosis caused by HIP1 ENTH deletion mutant with Akt/Dncasp9.

The effect of expression of a HIP1 dominant negative mutant on cellular survival was next investigated. At the molecular level, the dominant negative mutant of HIP1 (HIP1/deltaE lacking the ENTH domain) promoted cell death but expression of wild type HIP1 (FLHIP1) or vector alone (pcDNA3) did not induce cell death (FIG. 6b). 39% of HIP1/ DE-expressing cells and 50% of caspase 9-expressing cells were apoptotic. FIG. 12 shows the correction of HIP1 deltaE apoptosis by the expression fall length HIP1 (FLPHIP1). FIG. 13 shows the correction of apoptosis by the expression of dominant negative caspase 9 (DN Casp 9) and constitutatively active Akt (Myr-AKT) but not dominant negative caspase 8 (DN I-FLICE) or activated ras (Ras-V12). Expression of the endogenous HIP1, wild type HIP1, HIP1/DE and Caspase 9 was documented by Western blot analysis as shown in the bottom of FIG. 6b.

Example 4

HIP1 Transgenic Mice

This Example describes the construction of several HIP1 transgenic mice lines.

A. Generation of HIP1-Knockout Mice

This Example describes the inactivation of HIP1 by the replacement of exons 2 to 7 with a neomycin resistance gene (neo$^r$). The HIP1 knockout vector (pHIP1KO) was constructed from two mouse genomic clones. Mouse genomic clones were obtained using information from the human genomic structure deduced from the human genomic sequence of the long arm of chromosome 7 (GenBank accession no. AC004491) and the cDNA sequence (Genbank accession no. HSHIP1PRO). The mouse genomic clones were isolated from a 129/Sv genomic BAC library for subcloning and restriction mapping. The mouse cDNA used to screen for the genomic clones was obtained by homology screening from a fetal mouse cDNA library (provided by Lewis Chodosh, University of Pennsylvania). This cDNA was also used to deduce the 5' end of the HIP1 cDNA gene and promoter region. A restriction map of the 5' end of the gene as one of the HIP1 BAC clones contained exon 2 and the other contained exons 3 to 8. Using these two clones, the targeting vector, pHIP1KO, including the knockout region of approximately 13.7 kb (including exons 2 to 7), was completed. The most 5' HIP1 subclone (subclone EcoB/E) was digested with XbaI, filled in, and digested with XhoI. The resultant 3.5-kb fragment containing intronic sequence 500 bp upstream of the 5' arm was cloned into the NheI (blunted)-XhoI site of 38LoxPNeo (a modified version of pGT-N38 from New England Biolabs) that has a LoxpNeo cassette cloned into the polylinker. As a result, the 3.5-kb 5' arm was just 5' of the LoxPNeo cassette. This intermediate vector was then digested with XbaI located 3' to the Neo cassette and blunted. A subclone (H/B) that contained exon 8 and flanking 5' and 3' intronic sequences was digested with HindIII (the 4.0-kb 3' arm), which released the entire 4 kb of this subclone. This HindIII fragment was then blunted and ligated with the XbaI (blunted) intermediate vector. The 5' junction of this resultant vector was sequenced to determine if the 4-kb 3' arm was in the correct orientation. The final targeting vector was electroporated into 129SvJ RW1 ES cells (Incyte Genomics, St. Louis, Mo.), selected for G418 resistance, and screened by Southern blotting for correctly targeted clones. Generation of chimeric mice and germline transmission of the mutant allele were achieved using standard techniques. Briefly, The correctly targeted ES cell clone was injected into C57BL/6 blastocysts. Chimeras with a high percentage of agouti were mated to C57BL/6 females, and F1 agouti pups were genotyped by Southern blotting. An equal distribution of wild-type and heterozygous mice among the agouti F1 animals was found (31_/− to 30_/_ animals). F1 heterozygotes were subsequently intercrossed to generate F2 animals, which were genotyped at 3 weeks of age.

Tail biopsies of 3-week-old mice were performed at weaning. Genomic DNA was isolated using the Promega Wizard kit as specified by the manufacturer digested with EcoRI overnight, and run on a 0.7% agarose-Tris-borate EDTA (TBE) gel to separate 16.5-kb (wild type) and 12.0-kb (recombinant) bands detected with the 5' probe. The gel was then blotted onto Hybond-N filter (Amersham-Pharmacia) and blocked in 20 µg of salmon sperm DNA per ml in hybridization buffer (Amersham-Pharmacia) for 3 h at 65° C. 32 P labeling of the 5' probe was done by random-primed labeling (Roche) with [32 P]dCTP (NEN). The blots were then hybridized for 14 to 20 h at 65° C., washed twice in 2× SSC (1× SSC is 0.15 M NaCl plus 0.015 M sodium citrate) for 20 min and twice in 1× SSC for 10 min, and imaged on Kodak Biomax film.

Figure 18:
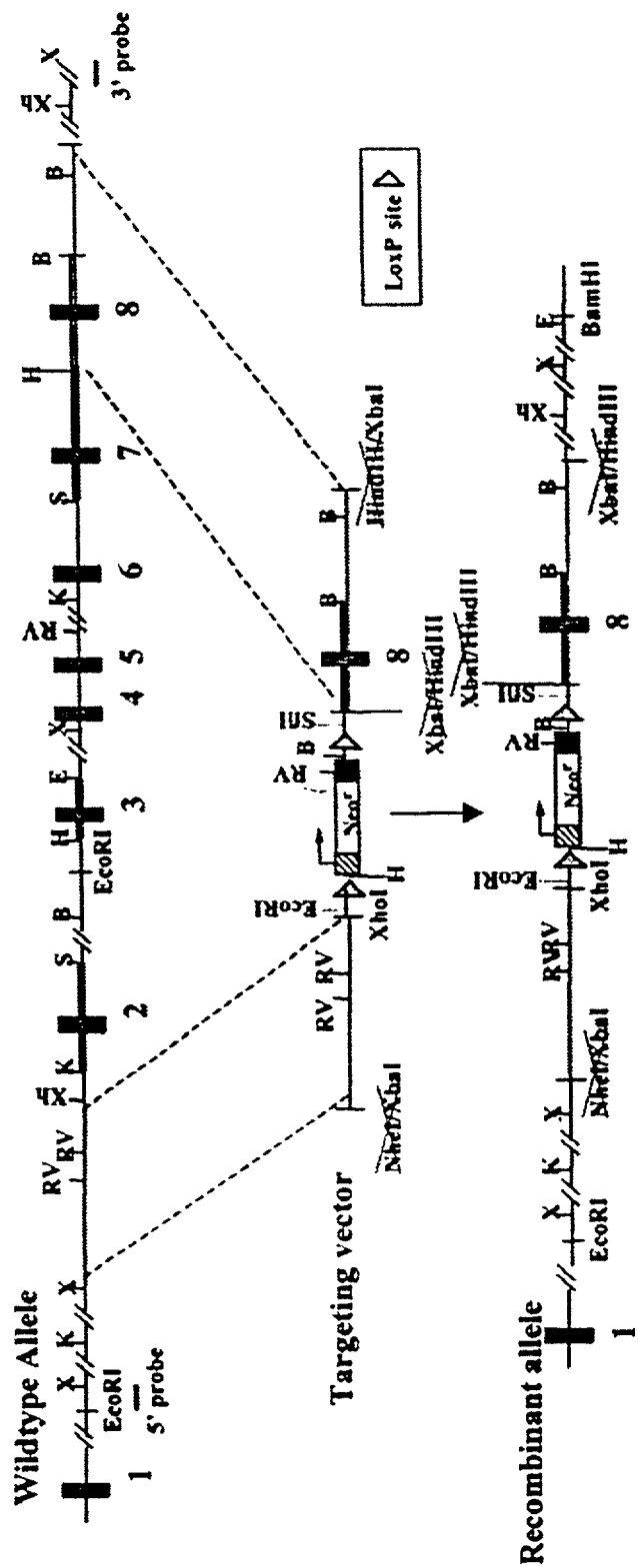
FIG. 18 shows the vector construction strategy for the HIP1 knock-out vector pHIP1KO.

During the construction of the targeting vector to knock out HIP1, a human HIP1 cDNA clone was used to screen a mouse embryonic cDNA library and a 5' murine HIP1 clone was isolated. This CDNA clone carried a new exon not previously described. By homology searching, a high-probability match with a 161-bp region of human chromosome 7q11 (BAC clone CTB-139P11) was identified (FIG. 18). The first intron separating this newly identified first exon and the second exon spans 139.5 kb. Exon 2 was previously designated exon 1 (Kalchman et al., Nat. Gent. 16:44 [1997]). Unlike exon 2, the newly discovered exon 1 contains a cluster of three in-frame ATG sequences, at +41, +50, and +62 in exon 1, with strong Kozak consensus sequences. Initiation of translation from the first ATG sequence would result in a HIP1 protein of 116 kDa, consistent with the size observed by Western blot analysis. Examination of the genomic sequence from BAC clone CTB-139P11 demonstrates a putative promoter region in the 5'-flanking sequence of the open reading frame that begins with HIP1 exon 1. This region contains a CCAAT box at −71 (FIG. 18) of exon 1 as well as several GC-rich areas corresponding to GC boxes (FIG. 18). Furthermore, several putative binding sites for transcription factors were found in this 5'-flanking region, including those for NF-κB, EGR-1, and c-myb. The predicted protein sequence for exon 1 encodes an additional 42 amino acids, compared with the sequence recorded at the National Center for Biotechnology Information (accession no. XP 004910). Analysis of the predicted protein sequence for full length HIP1 demonstrates a putative P-4,5-P2 and PI-3,4,5-P3 binding ENTH motif, in addition to putative clathrin and AP2 binding sequences, a leucine zipper, and a TALIN homology domain. The leucine zipper lies within a region that demonstrates homology to the central rod region of intermediate filament proteins.

B. HIP1 Knock-In

Figure 15:
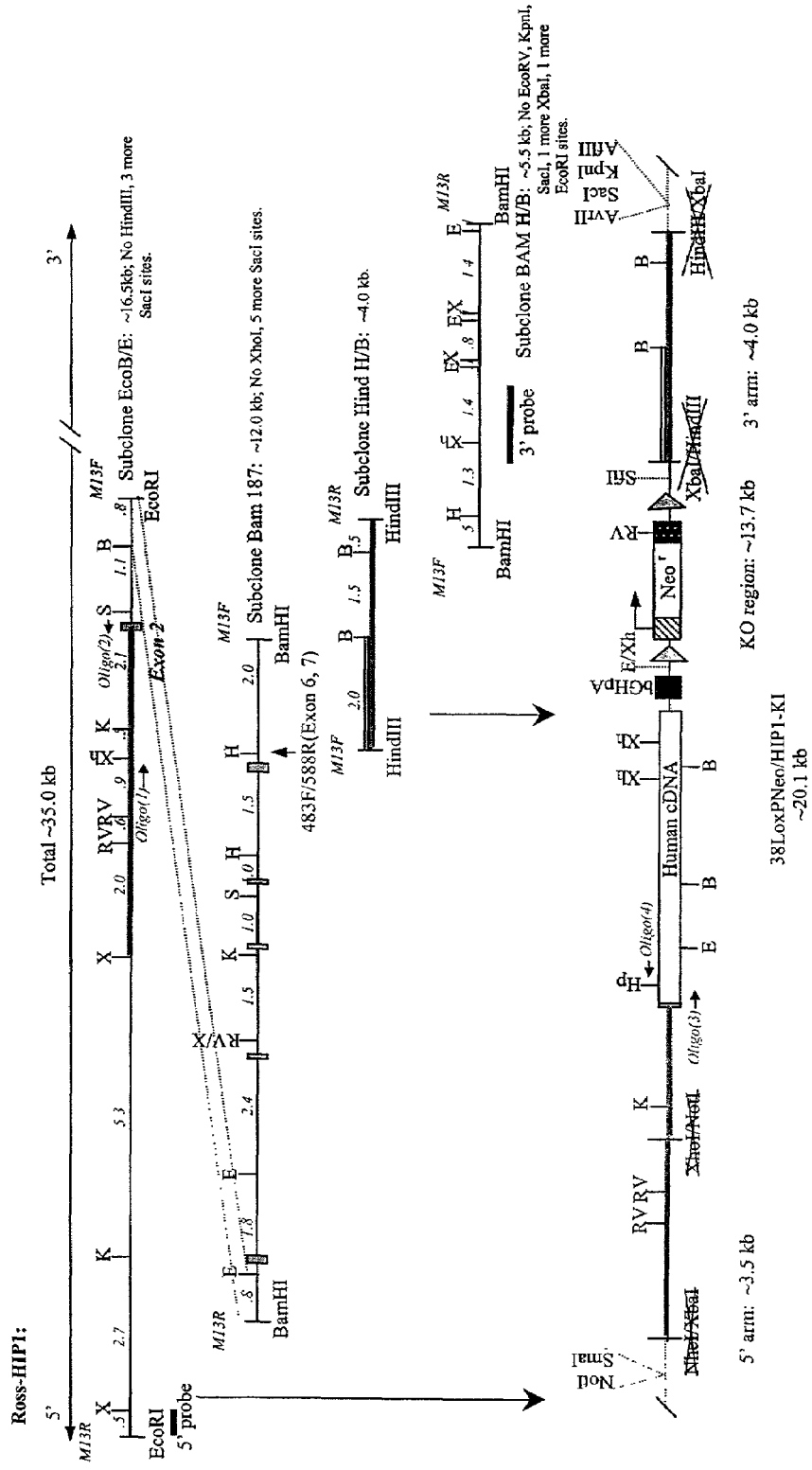
Figure 19:
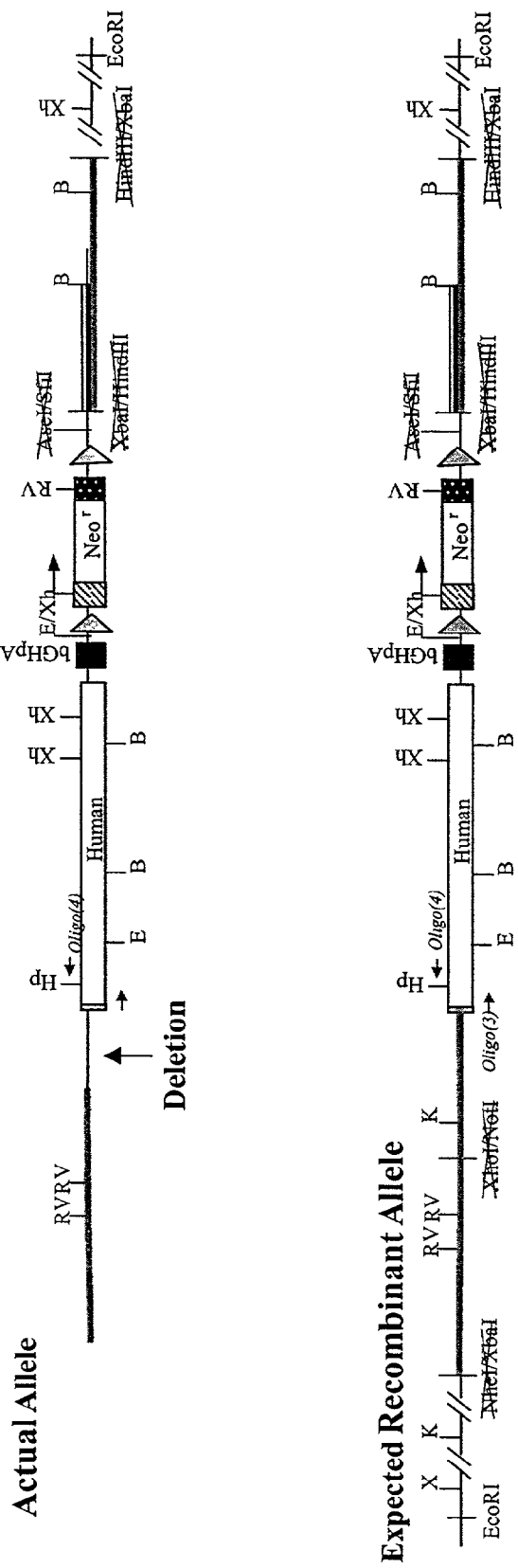
FIG. 19 shows the deletion of the HIP1/PDGFβR knock-in ES cell allele.

An additional transgenic mouse was constructed that had the HIP1 gene inactivated by a knock-in of exogenous DNA. FIG. 15 gives an overview of the construction of the vector. The vector (HIP1/PDGFβKI) was constructed by:
1. resequence 38LoxPNeo/HIP1 construct (See Section A above) with NeoR, choose sequence outside XhoI site to go 3' (primer 1). Primer 2 is from human cDNA, the same as 156R. Primer 3 is from human cDNA 157F, 5'-GCT GTA AAG GAA AAA CAC GCC-3' (SEQ ID NO: 5). Primer 4 is from human cDNA, the same as 588R.
2. Perform PCR reaction: Template: subclone EcoB/E; Primers: (1) and (2)
   Blunt-end PCR fragment~2.5 kb
   Digest with XhoI
3. Perform PCR reaction: Template: pcDNA3.HIP/P; Primers: (3) and (4)
   Blunt-end PCR fragment~0.4 kb
4. Digest ASIL vector with SacI+AscI, elute~2.1 kb bGHpA-loxPNeo fragment
   Digest pGL-1 with SacI+AscI
   Ligate
   Obtain plasmid pGL-1/step4, insert~2.1 kb
5. Three fragment ligation: pGL-1/Step4 digested with SalI+Ecl136I
   PCR fragment from step 2
   PCR fragment form step 3
   Obtain plasmid pGL-1/step5, insert~5.0 kb
6. Digest pcDNA3.HIP/P with NotI-blunt end+HpaI, elute~3.6 kb fragment
   Digest plasmid pGL-1/step with HpaI
   Ligate
   Obtain plasmid pGL-1/step6, insert~8.6 kb
7. Digest pGL-1/step6 with NotI+AscI, blunt-end, elute~8.6 kb fragment
   Digest 38LoxPNeo/HIP1 with XhoI+SfiI, blunt-end
   Ligate
   Obtain KI vector, total size~18.9 kb Embryonic stem (ES) cells were electroporated and screened for correct targeting using two DNA probes, one complementary to a 5' region and one complementary to a 3' region. DNA was digested with restriction enzymes and probed. Wild-type and mutant give different sized restriction fragments that were identified with the probes. One of the ES cells had a 248 bp deletion of parts of exon 2 and intron 1 (FIG. 19). Transgenic mice were also generated from the construct.

Targeted ES cells were then injected into blastocysts that were then impregnated into pseudopregnant females. The resultant chimeras were then bred to make F1s. The F1 generation is crossed onto various cre backgrounds.

C. Conditional Knock-Out Mouse

Figure 16:
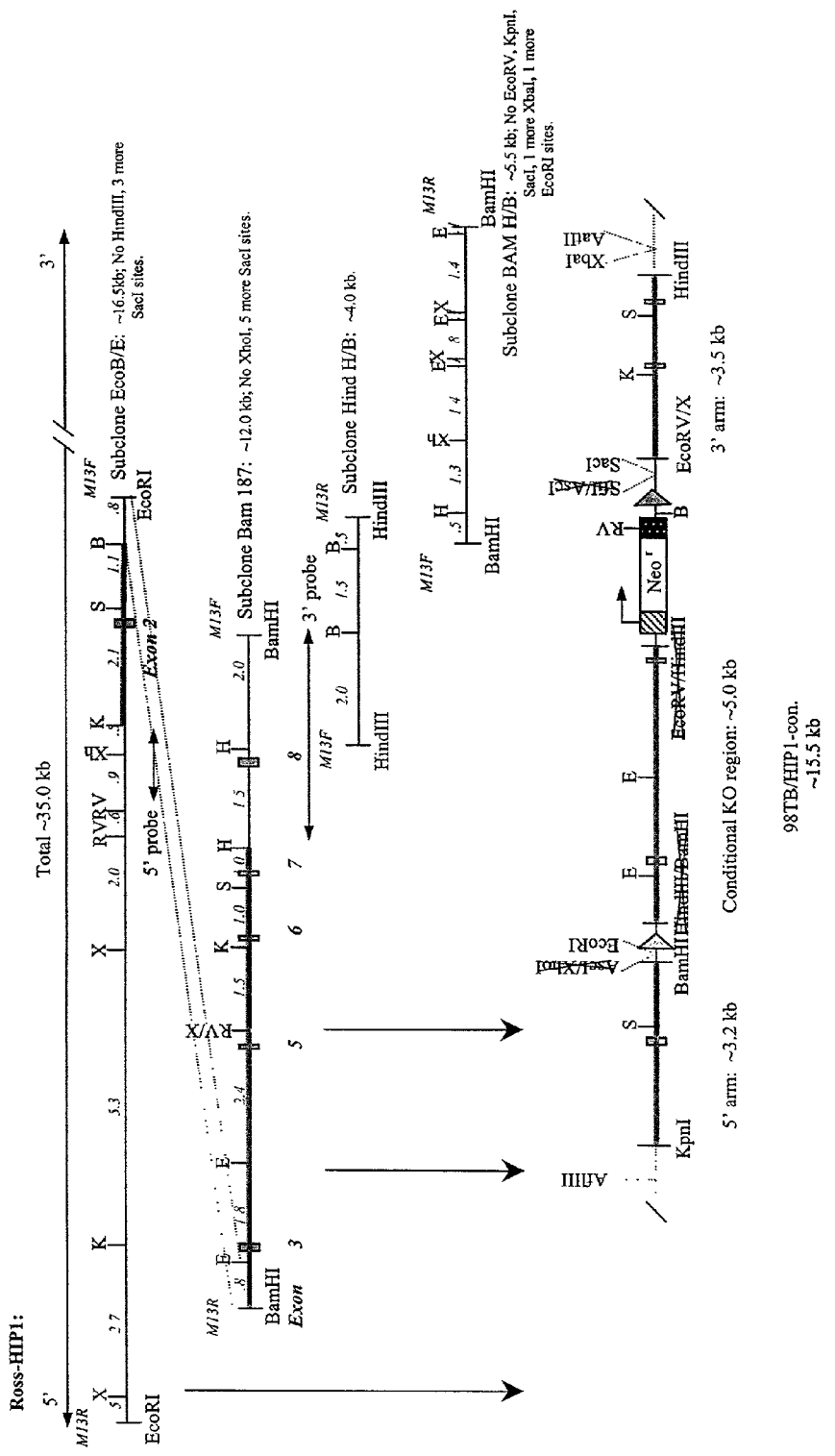
FIG. 16 shows the vector construction strategy for HIP1 conditional knock-out.

The Example describes the construction of a conditional HIP1 knock-out transgenic mouse. Infection of the mouse with an adenoviral vector expressing the cre gene will acutely decrease the levels of HIP1 via recombination. An overview of the cloning strategy is described in FIG. 16. The cloning strategy was as follows:
1. Clone 3.2 kb KpnI-BamHI fragment (5' homologous arm) into 98TB/KpnI+BamHI digestion.
   Obtain plasmid Step1~5.2 kb.
2. Clone 3.5 kb EcoRV-HindIII fragment (3' homologous arm) into plasmid Step 1/EcoRV+HindIII digestion.
   Obtain plasmid Step2~8.7 kb.
3. Clone 5.0 kb BamHI (blunt end)-EcoRV fragment (conditional KO region) into 38LoxPNeo/HindIII (blunt end) digestion.

Screen for correct orientation.
Obtain plasmid Step3~9.7 kb.
4. Clone 6.8 kb XhoI (blunt end)-SfiI (blunt end) fragment (conditional KO-Neo) from plasmid Step3 into plasmid Step2/AscI (blunt end) digestion.
Screen for correct orientation.
Obtain conditional KO vector~15.5 kb.

Transgenic mice were generated as described in section B above.

Example 5

Drug Screening

This Example describes exemplary drug screening methods suitable for screening compounds for HIP1 inhibitory activity. A high throughput screening method is utilized.

A. Embryonic Fibroblast Screening

HIP1+embryonic fibroblasts are obtained from wild-type mice and HIP1−/−embryonic fibroblasts are obtained from HIP1 knockout mice (Rao et al., Mol Cell Biol 21:7796 [2001]). These fibroblasts are cultured and libraries of therapeutic compounds are added to the cultures. Specific inhibitors of HIP1 are then identified as compounds that kill the HIP1+fibroblasts but not the HIP1−fibroblasts.

B. Cancer Cell Line Screeing

Drug screens are also performed using HIP1 expressing cell lines and HIP1 non-expressing colo205 cells (ATCC, obtained from a patient with metastatic colon cancer). The two cell lines are cultured in the presence of a library of therapeutic compounds. Compounds are identified that kill HIP1+ but not HIP1−cell lines.

We claim:

1. A method for characterizing prostate cancer in a subject, comprising:
   a) providing a biopsy tumor tissue sample from a subject, wherein said subject has been diagnosed with prostate cancer; and
   b) characterizing said biopsy tumor tissue sample by detecting the presence or absence of HIP1 in said sample with a nucleic acid probe configured to hybridize to a HIP1 nucleic acid sequence consisting of the nucleic acid sequence of SEQ ID NO:1, wherein said absence of HIP1 in said sample is indicative of one or more of properties of said cancer selected from the group consisting of PSA recurrence and recurrence free survival.

2. The method of claim 1, wherein said detecting HIP1 comprises detecting the presence of HIP1 mRNA.

3. The method of claim 1, wherein said detecting the presence of HIP1 mRNA comprises a detection assay selected from the group consisting of a Northern blot, in situ hybridization, reverse-transcriptase polymerase chain reaction, and microarray analysis.

4. The method of claim 1, wherein said probe is a primer.

* * * * *

```
                              SEQUENCE LISTING

<160> NUMBER OF SEQ ID NOS: 6

<210> SEQ ID NO 1
<211> LENGTH: 4534
<212> TYPE: DNA
<213> ORGANISM: Homo sapiens
<220> FEATURE:
<221> NAME/KEY: misc_feature
<222> LOCATION: (4521)..(4521)
<223> OTHER INFORMATION: The nucleotide "n" can be either a,t,c, or g
<221> NAME/KEY: misc_feature
<222> LOCATION: (4522)..(4522)
<223> OTHER INFORMATION: The nucleotide "n" can be either a,t,c, or g

<400> SEQUENCE: 1
ccaagcttgg taccccggg gcagccgagg gccctgact cggctcctcg cggcgacatg       60
gatcggatgg ccagctccat gaagcaggtg cccaacccac tgcccaaggt gctgagccgg     120
cgcggggtcg gcgctgggct ggaggcggcg gagcgcgaga gcttcgagcg gactcagact    180
gtcagcatca ataaggccat taatacgcag gaagtggctg taaaggaaaa acacgccaga    240
acgtgcatac tgggcaccca ccatgagaaa ggggcacaga ccttctggtc tgttgtcaac    300
cgcctgcctc tgtctagcaa cgcagtgctc tgctggaagt tctgccatgt gttccacaaa    360
ctcctccgag atggacaccc gaacgtcctg aaggactctc tgagatacag aaatgaattg    420
agtgacatga gcaggatgtg gggctacctg agcgaggggt atggccagct gtgcagcatc    480
tacctgaaac tgctaagaac caagatggag taccacacca aaaatcccag gttcccaggc    540
aacctgcaga tgagtgaccg ccagctggac gaggctggag aaagtgacgt gaacaacttt    600
tcccagttaa cagtggagat gttgactac ctggagtgtg aactcaacct cttccaaaca    660
gtattcaact ccctggacat gtcccgctct gtgtccgtga cggcagcagg gcagtgccgc    720
ctcgccccgc tgatccaggt catcttggac tgcagccacc tttatgacta cactgtcaag    780
cttctcttca aactccactc ctgcctccca gctgacaccc tgcaaggcca ccgggaccgc    840
ttcatggagc agtttacaaa gttgaaagat ctgttctacc gctccagcaa cctgcagtac    900
ttcaagcggc tcattcagat cccccagctg cctgagaacc cacccaactt cctgcgagcc    960
tcagccctgt cagaacatat cagccctgtg gtggtgatcc ctgcagaggc ctcatccccc   1020
gacagcgagc cagtcctaga gaaggatgac ctcatggaca tggatgcctc tcagcagaat   1080
ttatttgaca acaagtttga tgacatcttt ggcagttcat tcagcagtga tccttcaat   1140
```

```
ttcaacagtc aaaatggtgt gaacaaggat gagaaggacc acttaattga gcgactatac    1200
agagagatca gtggattgaa ggcacagcta gaaaacatga agactgagag ccagcgggtt    1260
gtgctgcagc tgaagggcca cgtcagcgag ctggaagcag atctggccga gcagcagcac    1320
ctgcggcagc aggcggccga cgactgtgaa ttcctgcggg cagaactgga cgagctcagg    1380
aggcagcggg aggacaccga gaaggctcag cggagcctgt ctgagataga aaggaaagct    1440
caagccaatg aacagcgata tagcaagcta aaggagaagt acagcgagct ggttcagaac    1500
cacgctgacc tgctgcggaa gaatgcgagg gtgaccaaac aggtgtccat ggccagacaa    1560
gcccaggtag atttggaacg agagaaaaaa gagctggagg attcgttgga gcgcatcagt    1620
gaccagggcc agcggaagac tcaagaacag ctggaagttc tagagagctt gaagcaggaa    1680
cttgccacaa gccaacggga gcttcaggtt ctgcaaggca gcctggaaac ttctgcccag    1740
tcagaagcaa actgggcagc cgagttcgcc gagctagaga aggagcggga cagcctggtg    1800
agtggcgcag ctcataggga ggaggaatta tctgctcttc ggaaagaact gcaggacact    1860
cagctcaaac tggccagcac agaggaatct atgtgccagc ttgccaaaga ccaacgaaaa    1920
atgcttctgg tggggtccag gaaggctgcg gagcaggtga tacaagacgc cctgaaccag    1980
cttgaagaac ctcctctcat cagctgcgct gggtctgcag atcacctcct ctccacggtc    2040
acatccattt ccagctgcat cgagcaactg gagaaaagct ggagccagta tctggcctgc    2100
ccagaagaca tcagtggact tctccattcc ataaccctgc tggcccactt gaccagcgac    2160
gccattgctc atggtccac cacctgcctc agagccccac ctgagcctgc cgactcactg    2220
accgaggcct gtaagcagta tggcagggaa accctcgcct acctggcctc cctggaggaa    2280
gagggaagcc ttgagaatgc cgacagcaca gccatgagga actgcctgag caagatcaag    2340
gccatcggcg aggagctcct gcccagggga ctggacatca gcaggagga ctggggggac    2400 ctggtggaca aggagatggc ggccacttca gctgctattg aaactgccac ggccagaata    2460
gaggagatgc tcagcaaatc ccgagcagga gacacaggag tcaaattgga ggtgaatgaa    2520
aggatccttg gttgctgtac cagcctcatg caagctattc aggtgctcat cgtggcctct    2580
aaggacctcc agagagagat tgtggagagc ggcagggta cagcatcccc taaagagttt    2640
tatgccaaga actctcgatg gacagaagga cttatctcag cctccaaggc tgtgggctgg    2700
ggagccactg tcatggtgga tgcagctgat ctggtggtac aaggcagagg gaaatttgag    2760
gagctaatgg tgtgttctca tgaaattgct gctagcacag cccagcttgt ggctgcatcc    2820
aaggtgaaag ctgataagga cagccccaac ctagcccagc tgcagcaggc ctctcgggga    2880
gtgaaccagg ccactgccgg cgttgtggcc tcaaccattt ccggcaaatc acagatcgaa    2940
gagacagaca acatggactt ctcaagcatg acgctgacac agatcaaacg ccaagagatg    3000
gattctcagg ttagggtgct agagctagaa aatgaattgc agaaggagcg tcaaaaactg    3060
ggagagcttc ggaaaaagca ctacgagctt gctggtgttg ctgagggctg ggaagaagga    3120
acagaggcat ctccacctac actgcaagaa gtggtaaccg aaaaagaata gagccaaacc    3180
aacaccccat atgtcagtgt aaatccttgt tacctatctc gtgtgtgtta tttccccagc    3240
cacaggccaa atccttggag tcccaggggc agcacacca ctgccattac ccagtgccga    3300
ggacatgcat gacacttcca aagactccct ccatagcgac accctttctg tttggaccca    3360
tggatttcca ctgcttctta tggtggttgg ttgggttttt tggttttgtt ttttttttttt    3420 aagtttcact cacatagcca actctcccaa agggcacacc cctggggctg agtctccagg    3480
```

-continued

```
gcccccccaac tgtggtagct ccagcgatgg tgctgcccag gcctctcggt gctccatctc    3540
cgcctccaca ctgaccaagt gctggccacc ccagtccatg ctccagggtc aggcggagct    3600
gctgagtgac agcttttcctc aaaaagcaga aggagagtga gtgcctttcc ctcctaaagc    3660
tgaatcccgg cggaaagcct ctgtccgcct ttacaaggga gaagacaaca gaaagaggga    3720
caagagggtt cacacagccc agttcccgtg acgaggctca aaaacttgat cacatgcttg    3780
aatggagctg gtgagatcaa caacactact tccctgccgg aatgaactgt ccgtgaatgg    3840
tctctgtcaa gcgggccgtc tcccttggcc cagagacgga gtgtgggagt gattcccaac    3900
tcctttctgc agacgtctgc cttggcatcc tcttgaatag gaagatcgtt ccaccttcta    3960
cgcaattgac aaacccggaa gatcagatgc aattgctccc atcagggaag aaccctatac    4020
ttggtttgct acccttagta tttattacta acctcccctta agcagcaaca gcctacaaag    4080
agatgcttgg agcaatcaga acttcaggtg tgactctagc aaagctcatc tttctgcccg    4140
gctacatcag ccttcaagaa tcagaagaaa ggccaaggtg ctggactgtt actgacttgg    4200
atcccaaagc aaggagatca tttggagctc ttgggtcaga gaaaatgaga aggacagag     4260 ccagcggctc caactccttt cagccacatg ccccaggctc tcgctgccct gtggacagga    4320
tgaggacaga gggcacatga acagcttgcc agggatgggc agcccaacag cacttttcct    4380
cttctagatg gaccccagca tttaagtgac cttctgatct tgggaaaaca gcgtcttcct    4440
tctttatcta tagcaactca ttggtggtag ccatcaagca cttcggaatt cctgcagccc    4500
gggcggccgc tcgagcatgc nntagagggc ccta                                4534
```

<210> SEQ ID NO 2
<211> LENGTH: 1475
<212> TYPE: PRT
<213> ORGANISM: Homo sapiens
<220> FEATURE:
<221> NAME/KEY: misc_feature
<222> LOCATION: (1472)..(1472)
<223> OTHER INFORMATION: The amino acid "X" can be any amino acid
<400> SEQUENCE: 2

```
Met Asp Arg Met Ala Ser Ser Met Lys Gln Val Pro Asn Pro Leu Pro
1               5                   10                  15

Lys Val Leu Ser Arg Arg Gly Val Gly Ala Gly Leu Glu Ala Ala Glu
            20                  25                  30

Arg Glu Ser Phe Glu Arg Thr Gln Thr Val Ser Ile Asn Lys Ala Ile
        35                  40                  45

Asn Thr Gln Glu Val Ala Val Lys Glu Lys His Ala Arg Thr Cys Ile
    50                  55                  60

Leu Gly Thr His His Glu Lys Gly Ala Gln Thr Phe Trp Ser Val Val
65                  70                  75                  80

Asn Arg Leu Pro Leu Ser Ser Asn Ala Val Leu Cys Trp Lys Phe Cys
                85                  90                  95

His Val Phe His Lys Leu Leu Arg Asp Gly His Pro Asn Val Leu Lys
            100                 105                 110

Asp Ser Leu Arg Tyr Arg Asn Glu Leu Ser Asp Met Ser Arg Met Trp
        115                 120                 125

Gly Tyr Leu Ser Glu Gly Tyr Gly Gln Leu Cys Ser Ile Tyr Leu Lys
    130                 135                 140

Leu Leu Arg Thr Lys Met Glu Tyr His Thr Lys Asn Pro Arg Phe Pro
145                 150                 155                 160

Gly Asn Leu Gln Met Ser Asp Arg Gln Leu Asp Glu Ala Gly Glu Ser
```

-continued

```
                165                 170                 175
Asp Val Asn Asn Phe Ser Gln Leu Thr Val Glu Met Phe Asp Tyr Leu
            180                 185                 190
Glu Cys Glu Leu Asn Leu Phe Gln Thr Val Phe Asn Ser Leu Asp Met
            195                 200                 205
Ser Arg Ser Val Ser Val Thr Ala Ala Gly Gln Cys Arg Leu Ala Pro
            210                 215                 220
Leu Ile Gln Val Ile Leu Asp Cys Ser His Leu Tyr Asp Tyr Thr Val
225                 230                 235                 240
Lys Leu Leu Phe Lys Leu His Ser Cys Leu Pro Ala Asp Thr Leu Gln
                245                 250                 255
Gly His Arg Asp Arg Phe Met Glu Gln Phe Thr Lys Leu Lys Asp Leu
                260                 265                 270
Phe Tyr Arg Ser Ser Asn Leu Gln Tyr Phe Lys Arg Leu Ile Gln Ile
                275                 280                 285
Pro Gln Leu Pro Glu Asn Pro Asn Phe Leu Arg Ala Ser Ala Leu
                290                 295                 300
Ser Glu His Ile Ser Pro Val Val Ile Pro Ala Glu Ala Ser Ser
305                 310                 315                 320
Pro Asp Ser Glu Pro Val Leu Glu Lys Asp Asp Leu Met Asp Met Asp
                325                 330                 335
Ala Ser Gln Gln Asn Leu Phe Asp Asn Lys Phe Asp Ile Phe Gly
                340                 345                 350
Ser Ser Phe Ser Ser Asp Pro Phe Asn Phe Asn Ser Gln Asn Gly Val
            355                 360                 365
Asn Lys Asp Glu Lys Asp His Leu Ile Glu Arg Leu Tyr Arg Glu Ile
370                 375                 380
Ser Gly Leu Lys Ala Gln Leu Glu Asn Met Lys Thr Glu Ser Gln Arg
385                 390                 395                 400
Val Val Leu Gln Leu Lys Gly His Val Ser Glu Leu Glu Ala Asp Leu
                405                 410                 415
Ala Glu Gln Gln His Leu Arg Gln Gln Ala Ala Asp Asp Cys Glu Phe
                420                 425                 430
Leu Arg Ala Glu Leu Asp Glu Leu Arg Arg Gln Arg Glu Asp Thr Glu
            435                 440                 445
Lys Ala Gln Arg Ser Leu Ser Glu Ile Glu Arg Lys Ala Gln Ala Asn
            450                 455                 460
Glu Gln Arg Tyr Ser Lys Leu Lys Glu Lys Tyr Ser Glu Leu Val Gln
465                 470                 475                 480
Asn His Ala Asp Leu Leu Arg Lys Asn Ala Glu Val Thr Lys Gln Val
                485                 490                 495
Ser Met Ala Arg Gln Ala Gln Val Asp Leu Glu Arg Glu Lys Lys Glu
            500                 505                 510
Leu Glu Asp Ser Leu Glu Arg Ile Ser Asp Gln Gly Gln Arg Lys Thr
            515                 520                 525
Gln Glu Gln Leu Glu Val Leu Glu Ser Leu Lys Gln Glu Leu Ala Thr
            530                 535                 540
Ser Gln Arg Glu Leu Gln Val Leu Gln Gly Ser Leu Glu Thr Ser Ala
545                 550                 555                 560
Gln Ser Glu Ala Asn Trp Ala Ala Glu Phe Ala Glu Leu Glu Lys Glu
                565                 570                 575
Arg Asp Ser Leu Val Ser Gly Ala Ala His Arg Glu Glu Glu Leu Ser
                580                 585                 590
```

```
Ala Leu Arg Lys Glu Leu Gln Asp Thr Gln Leu Lys Leu Ala Ser Thr
            595                 600                 605

Glu Glu Ser Met Cys Gln Leu Ala Lys Asp Gln Arg Lys Met Leu Leu
            610                 615                 620

Val Gly Ser Arg Lys Ala Ala Glu Gln Val Ile Gln Asp Ala Leu Asn
625                 630                 635                 640

Gln Leu Glu Glu Pro Pro Leu Ile Ser Cys Ala Gly Ser Ala Asp His
            645                 650                 655

Leu Leu Ser Thr Val Thr Ser Ile Ser Ser Cys Ile Glu Gln Leu Glu
            660                 665                 670

Lys Ser Trp Ser Gln Tyr Leu Ala Cys Pro Glu Asp Ile Ser Gly Leu
            675                 680                 685

Leu His Ser Ile Thr Leu Leu Ala His Leu Thr Ser Asp Ala Ile Ala
            690                 695                 700

His Gly Ala Thr Thr Cys Leu Arg Ala Pro Glu Pro Ala Asp Ser
705                 710                 715                 720

Leu Thr Glu Ala Cys Lys Gln Tyr Gly Arg Glu Thr Leu Ala Tyr Leu
            725                 730                 735

Ala Ser Leu Glu Glu Glu Gly Ser Leu Glu Asn Ala Asp Ser Thr Ala
            740                 745                 750

Met Arg Asn Cys Leu Ser Lys Ile Lys Ala Ile Gly Glu Glu Leu Leu
            755                 760                 765

Pro Arg Gly Leu Asp Ile Lys Gln Glu Glu Leu Gly Asp Leu Val Asp
            770                 775                 780

Lys Glu Met Ala Ala Thr Ser Ala Ala Ile Glu Thr Ala Thr Ala Arg
785                 790                 795                 800

Ile Glu Glu Met Leu Ser Lys Ser Arg Ala Gly Asp Thr Gly Val Lys
            805                 810                 815

Leu Glu Val Asn Glu Arg Ile Leu Gly Cys Cys Thr Ser Leu Met Gln
            820                 825                 830

Ala Ile Gln Val Leu Ile Val Ala Ser Lys Asp Leu Gln Arg Glu Ile
            835                 840                 845

Val Glu Ser Gly Arg Gly Thr Ala Ser Pro Lys Glu Phe Tyr Ala Lys
            850                 855                 860

Asn Ser Arg Trp Thr Glu Gly Leu Ile Ser Ala Ser Lys Ala Val Gly
865                 870                 875                 880

Trp Gly Ala Thr Val Met Val Asp Ala Ala Asp Leu Val Val Gln Gly
            885                 890                 895

Arg Gly Lys Phe Glu Glu Leu Met Val Cys Ser His Glu Ile Ala Ala
            900                 905                 910

Ser Thr Ala Gln Leu Val Ala Ala Ser Lys Val Lys Ala Asp Lys Asp
            915                 920                 925

Ser Pro Asn Leu Ala Gln Leu Gln Gln Ala Ser Arg Gly Val Asn Gln
            930                 935                 940

Ala Thr Ala Gly Val Val Ala Ser Thr Ile Ser Gly Lys Ser Gln Ile
945                 950                 955                 960

Glu Glu Thr Asp Asn Met Asp Phe Ser Ser Met Thr Leu Thr Gln Ile
            965                 970                 975

Lys Arg Gln Glu Met Asp Ser Gln Val Arg Val Leu Glu Leu Glu Asn
            980                 985                 990

Glu Leu Gln Lys Glu Arg Gln Lys Leu Gly Glu Leu Arg Lys Lys His
            995                 1000                1005
```

-continued

```
Tyr Glu Leu Ala Gly Val Ala Glu Gly Trp Glu Glu Gly Thr Glu
    1010                1015                1020

Ala Ser Pro Pro Thr Leu Gln Glu Val Val Thr Glu Lys Glu Ser
    1025                1030                1035

Gln Thr Asn Thr Pro Tyr Val Ser Val Asn Pro Cys Tyr Leu Ser
    1040                1045                1050

Arg Val Cys Tyr Phe Pro Ser His Arg Pro Asn Pro Trp Ser Pro
    1055                1060                1065

Arg Gly Ser His Thr Thr Ala Ile Thr Gln Cys Arg Gly His Ala
    1070                1075                1080

His Phe Gln Arg Leu Pro Pro Arg His Pro Phe Cys Leu Asp Pro
    1085                1090                1095

Trp Ile Ser Thr Ala Ser Tyr Gly Gly Trp Leu Gly Phe Leu Val
    1100                1105                1110

Leu Phe Phe Phe Phe Lys Phe His Ser His Ser Gln Leu Ser Gln
    1115                1120                1125

Arg Ala His Pro Trp Gly Val Ser Arg Ala Pro Gln Leu Trp Leu
    1130                1135                1140

Gln Arg Trp Cys Cys Pro Gly Leu Ser Val Leu His Leu Arg Leu
    1145                1150                1155

His Thr Asp Gln Val Leu Ala His Pro Val His Ala Pro Gly Ser
    1160                1165                1170

Gly Gly Ala Ala Glu Gln Leu Ser Ser Lys Ser Arg Arg Arg Val
    1175                1180                1185

Ser Ala Phe Pro Ser Ser Ile Pro Ala Glu Ser Leu Cys Pro Pro
    1190                1195                1200

Leu Gln Gly Arg Arg Gln Gln Lys Glu Gly Gln Glu Gly Ser His
    1205                1210                1215

Ser Pro Val Pro Val Thr Arg Leu Lys Asn Leu Ile Thr Cys Leu
    1220                1225                1230

Asn Gly Ala Gly Glu Ile Asn Asn Thr Thr Ser Leu Pro Glu Thr
    1235                1240                1245

Val Arg Glu Trp Ser Leu Ser Ser Gly Pro Ser Pro Leu Ala Gln
    1250                1255                1260

Arg Arg Ser Val Gly Val Ile Pro Asn Ser Phe Leu Gln Thr Ser
    1265                1270                1275

Ala Leu Ala Ser Ser Ile Gly Arg Ser Phe His Leu Leu Arg Asn
    1280                1285                1290

Gln Thr Arg Lys Ile Arg Cys Asn Cys Ser His Gln Gly Arg Thr
    1295                1300                1305

Leu Tyr Leu Val Cys Tyr Pro Tyr Leu Leu Leu Thr Ser Leu Lys
    1310                1315                1320

Gln Gln Gln Pro Thr Lys Arg Cys Leu Glu Gln Ser Glu Leu Gln
    1325                1330                1335

Val Leu Gln Ser Ser Ser Phe Cys Pro Ala Thr Ser Ala Phe Lys
    1340                1345                1350

Asn Gln Lys Lys Gly Gln Gly Ala Gly Leu Leu Leu Thr Trp Ile
    1355                1360                1365

Pro Lys Gln Gly Asp His Leu Glu Leu Leu Gly Gln Arg Lys Glu
    1370                1375                1380

Arg Thr Glu Pro Ala Ala Pro Thr Pro Phe Ser His Met Pro Gln
    1385                1390                1395

Ala Leu Ala Ala Leu Trp Thr Gly Gly Gln Arg Ala His Glu Gln
```

```
                     1400                 1405                1410
Leu Ala Arg Asp Gly Gln Pro Asn Ser Thr Phe Pro Leu Leu Asp
    1415                1420                1425

Gly Pro Gln His Leu Ser Asp Leu Leu Ile Leu Gly Lys Gln Arg
    1430                1435                1440

Leu Pro Ser Leu Ser Ile Ala Thr His Trp Trp Pro Ser Ser Thr
    1445                1450                1455

Ser Glu Phe Leu Gln Pro Gly Arg Pro Leu Glu His Ala Xaa Glu
    1460                1465                1470

Gly Pro
    1475

<210> SEQ ID NO 3
<211> LENGTH: 3911
<212> TYPE: DNA
<213> ORGANISM: Homo sapiens

<400> SEQUENCE: 3
gttaacagtg gagatgtttg actacctgga gtgtgaactc aacctcttcc aaacagtatt     60
caactccctg acatgtccc gctctgtgtc cgtgacggca gcagggcagt gccgcctcgc    120
cccgctgatc caggtcatct tggactgcag ccacctttat gactcactg tcaagcttct    180
cttcaaactc cactcctgcc tcccagctga cacctgcaa ggccaccggg accgcttcat    240
ggagcagttt acaaagttga agatctgtt ctaccgctcc agcaacctgc agtacttcaa    300
gcggctcatt cagatccccc agctgcctga gaacccaccc aacttcctgc gagcctcagc    360
cctgtcagaa catatcagcc ctgtggtggt gatccctgca gaggcctcat ccccgacag    420
cgagccagtc ctagagaagg atgacctcat ggacatggat gcctctcagc agaatttatt    480
tgacaacaag tttgatgaca tctttggcag ttcattcagc agtgatccct tcaatttcaa    540
cagtcaaaat ggtgtgaaca aggatgagaa ggaccactta attgagcgac atacagaga    600
gatcagtgga ttgaaggcac agctagaaaa catgaagact gagagccagc gggttgtgct    660
gcagctgaag ggccacgtca gcgagctgga agcagatctg ccgagcagc agcacctgcg    720
gcagcaggcg gccgacgact gtgaattcct gcgggcagaa ctggacgagc tcaggaggca    780
gcgggaggac accgagaagg ctcagcggag cctgtctgag atagaaagga aagctcaagc    840
caatgaacag cgatatagca agctaaagga gaagtacagc gagctggttc agaaccacgc    900
tgacctgctg cggaagaatg cagaggtgac caaacaggtg tccatggcca gacaagccca    960
ggtagatttg gaacgagaga aaaagagct ggaggattcg ttggagcgca tcagtgacca   1020
gggccagcgg aagactcaag aacagctgga agttctagag agcttgaagc aggaacttgc   1080
cacaagccaa cgggagcttc aggttctgca aggcagcctg aaacttctg cccagtcaga   1140
agcaaactgg gcagccgagt cgccgagct agagaaggag cgggacagcc tggtgagtgg   1200
cgcagctcat agggaggagg aattatctgc tcttcggaaa gaactgcagg acactcagct   1260
caaactggcc agcacagagg aatctatgtg ccagcttgcc aaagaccaac gaaaaatgct   1320
tctggtgggg tccaggaagg ctgcggagca ggtgatacaa gacgccctga accagcttga   1380
agaacctcct ctcatcagct gcgctgggtc tgcagatcac ctcctctcca cggtcacatc   1440
catttccagc tgcatcgagc aactggagaa aagctggagc cagtatctgg cctgcccaga   1500
agacatcagt ggacttctcc attccataac cctgctggcc cacttgacca gcgacgccat   1560
tgctcatggt gccaccacct gcctcagagc cccacctgag cctgccgact cactgaccga   1620
```

```
ggcctgtaag cagtatggca gggaaaccct cgcctacctg gcctccctgg aggaagaggg    1680
aagccttgag aatgccgaca gcacagccat gaggaactgc ctgagcaaga tcaaggccat    1740
cggcgaggag ctcctgccca ggggactgga catcaagcag gaggagctgg ggacctggt    1800
ggacaaggag atggcggcca cttcagctgc tattgaaact gccacggcca aatagagga    1860
gatgctcagc aaatcccgag caggagacac aggagtcaaa ttggaggtga atgaaaggat    1920
ccttggttgc tgtaccagcc tcatgcaagc tattcaggtg ctcatcgtgg cctctaagga    1980
cctccagaga gagattgtgg agagcggcag gggtacagca tcccctaaag agttttatgc    2040
caagaactct cgatggacag aaggacttat ctcagcctcc aaggctgtgg gctggggagc    2100
cactgtcatg gtggatgcag ctgatctggt ggtacaaggc agagggaaat ttgaggagct    2160
aatggtgtgt tctcatgaaa ttgctgctag cacagcccag cttgtggctg catccaaggt    2220
gaaagctgat aaggacagcc ccaacctagc ccagctgcag caggcctctc ggggagtgaa    2280
ccaggccact gccggcgttg tggcctcaac catttccggc aaatcacaga tcgaagagac    2340
agacaacatg gacttctcaa gcatgacgct gacacagatc aaacgccaag agatggattc    2400
tcaggttagg gtgctagagc tagaaaatga attgcagaag gagcgtcaaa aactgggaga    2460
gcttcggaaa aagcactacg agcttgctgg tgttgctgag ggctgggaag aaggaacaga    2520
ggcatctcca cctacactgc aagaagtggt aaccgaaaaa gaatagagcc aaaccaacac    2580
cccatatgtc agtgtaaatc cttgttacct atctcgtgtg tgttatttcc ccagccacag    2640
gccaaatcct tggagtccca ggggcagcca ccactgcc attacccagt gccgaggaca    2700
tgcatgacac ttccaaagac tccctccata gcgacaccct ttctgtttgg acccatggat    2760
ttccactgct tcttatggtg gttggttggg tttttggtt ttgtttttt tttttaagtt    2820
tcactcacat agccaactct cccaaagggc acacccctgg ggctgagtct ccagggcccc    2880
ccaactgtgg tagctccagc gatggtgctg cccaggcctc tcggtgctcc atctccgcct    2940
ccacactgac caagtgctgg cccacccagt ccatgctcca gggtcaggcg gagctgctga    3000
gtgacagctt tcctcaaaaa gcagaaggag agtgagtgcc tttccctcct aaagctgaat    3060
cccggcggaa agcctctgtc cgcctttaca agggagaaga caacagaaag agggacaaga    3120
gggttcacac agcccagttc ccgtgacgag gctcaaaaac ttgatcacat gcttgaatgg    3180
agctggtgag atcaacaaca ctacttccct gccggaatga actgtccgtg aatggtctct    3240
gtcaagcggg ccgtctccct tggcccagag acggagtgtg ggagtgattc ccaactcctt    3300
tctgcagacg tctgccttgg catcctcttg aataggaaga tcgttccacc ttctacgcaa    3360
ttgacaaacc cggaagatca gatgcaattg ctcccatcag ggaagaaccc tatacttggt    3420
ttgctaccct tagtatttat tactaacctc ccttaagcag caacagccta caaagagatg    3480
cttggagcaa tcagaacttc aggtgtgact ctagcaaagc tcatctttct gcccggctac    3540
atcagccttc aagaatcaga agaaaggcca aggtgctgga ctgttactga cttggatccc    3600
aaagcaagga gatcatttgg agctcttggg tcagagaaaa tgagaaagga cagagccagc    3660
ggctccaact cctttcagcc acatgcccca ggctctcgct gccctgtgga caggatgagg    3720
acagagggca catgaacagc ttgccaggga tgggcagccc aacagcactt ttcctcttct    3780
agatggaccc cagcatttaa gtgaccttct gatcttggga aaacagcgtc ttccttcttt    3840
atctatagca actcattggt ggtagccatc aagcacttcg gaattcctgc agcccgggcg    3900
gccgctcgag c                                                         3911
```

```
<210> SEQ ID NO 4
<211> LENGTH: 1283
<212> TYPE: PRT
<213> ORGANISM: Homo sapiens

<400> SEQUENCE: 4
```

| | | | | | | | | | | | | | | | |
|---|---|---|---|---|---|---|---|---|---|---|---|---|---|---|---|
| Met | Phe | Asp | Tyr | Leu | Glu | Cys | Glu | Leu | Asn | Leu | Phe | Gln | Thr | Val | Phe |
| 1 | | | | 5 | | | | | 10 | | | | | 15 | |
| Asn | Ser | Leu | Asp | Met | Ser | Arg | Ser | Val | Ser | Val | Thr | Ala | Ala | Gly | Gln |
| | | | 20 | | | | | 25 | | | | | 30 | | |
| Cys | Arg | Leu | Ala | Pro | Leu | Ile | Gln | Val | Ile | Leu | Asp | Cys | Ser | His | Leu |
| | | 35 | | | | | 40 | | | | | 45 | | | |
| Tyr | Asp | Tyr | Thr | Val | Lys | Leu | Leu | Phe | Lys | Leu | His | Ser | Cys | Leu | Pro |
| 50 | | | | | 55 | | | | | 60 | | | | | |
| Ala | Asp | Thr | Leu | Gln | Gly | His | Arg | Asp | Arg | Phe | Met | Glu | Gln | Phe | Thr |
| 65 | | | | | 70 | | | | | 75 | | | | | 80 |
| Lys | Leu | Lys | Asp | Leu | Phe | Tyr | Arg | Ser | Ser | Asn | Leu | Gln | Tyr | Phe | Lys |
| | | | | 85 | | | | | 90 | | | | | 95 | |
| Arg | Leu | Ile | Gln | Ile | Pro | Gln | Leu | Pro | Glu | Asn | Pro | Pro | Asn | Phe | Leu |
| | | | 100 | | | | | 105 | | | | | 110 | | |
| Arg | Ala | Ser | Ala | Leu | Ser | Glu | His | Ile | Ser | Pro | Val | Val | Ile | Pro |
| | | 115 | | | | | 120 | | | | | 125 | | | |
| Ala | Glu | Ala | Ser | Ser | Pro | Asp | Ser | Glu | Pro | Val | Leu | Glu | Lys | Asp | Asp |
| | 130 | | | | | 135 | | | | | 140 | | | | |
| Leu | Met | Asp | Met | Asp | Ala | Ser | Gln | Gln | Asn | Leu | Phe | Asp | Asn | Lys | Phe |
| 145 | | | | | 150 | | | | | 155 | | | | | 160 |
| Asp | Asp | Ile | Phe | Gly | Ser | Ser | Phe | Ser | Ser | Asp | Pro | Phe | Asn | Phe | Asn |
| | | | | 165 | | | | | 170 | | | | | 175 | |
| Ser | Gln | Asn | Gly | Val | Asn | Lys | Asp | Glu | Lys | Asp | His | Leu | Ile | Glu | Arg |
| | | | 180 | | | | | 185 | | | | | 190 | | |
| Leu | Tyr | Arg | Glu | Ile | Ser | Gly | Leu | Lys | Ala | Gln | Leu | Glu | Asn | Met | Lys |
| | | 195 | | | | | 200 | | | | | 205 | | | |
| Thr | Glu | Ser | Gln | Arg | Val | Val | Leu | Gln | Leu | Lys | Gly | His | Val | Ser | Glu |
| | 210 | | | | | 215 | | | | | 220 | | | | |
| Leu | Glu | Ala | Asp | Leu | Ala | Glu | Gln | Gln | His | Leu | Arg | Gln | Gln | Ala | Ala |
| 225 | | | | | 230 | | | | | 235 | | | | | 240 |
| Asp | Asp | Cys | Glu | Phe | Leu | Arg | Ala | Glu | Leu | Asp | Glu | Leu | Arg | Arg | Gln |
| | | | | 245 | | | | | 250 | | | | | 255 | |
| Arg | Glu | Asp | Thr | Glu | Lys | Ala | Gln | Arg | Ser | Leu | Ser | Glu | Ile | Glu | Arg |
| | | | 260 | | | | | 265 | | | | | 270 | | |
| Lys | Ala | Gln | Ala | Asn | Glu | Gln | Arg | Tyr | Ser | Lys | Leu | Lys | Glu | Lys | Tyr |
| | | 275 | | | | | 280 | | | | | 285 | | | |
| Ser | Glu | Leu | Val | Gln | Asn | His | Ala | Asp | Leu | Leu | Arg | Lys | Asn | Ala | Glu |
| | 290 | | | | | 295 | | | | | 300 | | | | |
| Val | Thr | Lys | Gln | Val | Ser | Met | Ala | Arg | Gln | Ala | Gln | Val | Asp | Leu | Glu |
| 305 | | | | | 310 | | | | | 315 | | | | | 320 |
| Arg | Glu | Lys | Lys | Glu | Leu | Glu | Asp | Ser | Leu | Glu | Arg | Ile | Ser | Asp | Gln |
| | | | | 325 | | | | | 330 | | | | | 335 | |
| Gly | Gln | Arg | Lys | Thr | Gln | Glu | Gln | Leu | Glu | Val | Leu | Glu | Ser | Leu | Lys |
| | | | 340 | | | | | 345 | | | | | 350 | | |
| Gln | Glu | Leu | Ala | Thr | Ser | Gln | Arg | Glu | Leu | Gln | Val | Leu | Gln | Gly | Ser |
| | | 355 | | | | | 360 | | | | | 365 | | | |
| Leu | Glu | Thr | Ser | Ala | Gln | Ser | Glu | Ala | Asn | Trp | Ala | Ala | Glu | Phe | Ala |
| | 370 | | | | | 375 | | | | | 380 | | | | |

-continued

```
Glu Leu Glu Lys Glu Arg Asp Ser Leu Val Ser Gly Ala Ala His Arg
385                 390                 395                 400

Glu Glu Glu Leu Ser Ala Leu Arg Lys Glu Leu Gln Asp Thr Gln Leu
            405                 410                 415

Lys Leu Ala Ser Thr Glu Glu Ser Met Cys Gln Leu Ala Lys Asp Gln
        420                 425                 430

Arg Lys Met Leu Leu Val Gly Ser Arg Lys Ala Ala Glu Gln Val Ile
            435                 440                 445

Gln Asp Ala Leu Asn Gln Leu Glu Glu Pro Leu Ile Ser Cys Ala
        450                 455                 460

Gly Ser Ala Asp His Leu Leu Ser Thr Val Thr Ser Ile Ser Ser Cys
465                 470                 475                 480

Ile Glu Gln Leu Glu Lys Ser Trp Ser Gln Tyr Leu Ala Cys Pro Glu
                485                 490                 495

Asp Ile Ser Gly Leu Leu His Ser Ile Thr Leu Leu Ala His Leu Thr
            500                 505                 510

Ser Asp Ala Ile Ala His Gly Ala Thr Thr Cys Leu Arg Ala Pro Pro
        515                 520                 525

Glu Pro Ala Asp Ser Leu Thr Glu Ala Cys Lys Gln Tyr Gly Arg Glu
530                 535                 540

Thr Leu Ala Tyr Leu Ala Ser Leu Glu Glu Gly Ser Leu Glu Asn
545                 550                 555                 560

Ala Asp Ser Thr Ala Met Arg Asn Cys Leu Ser Lys Ile Lys Ala Ile
                565                 570                 575

Gly Glu Glu Leu Leu Pro Arg Gly Leu Asp Ile Lys Gln Glu Leu
            580                 585                 590

Gly Asp Leu Val Asp Lys Glu Met Ala Ala Thr Ser Ala Ala Ile Glu
        595                 600                 605

Thr Ala Thr Ala Arg Ile Glu Glu Met Leu Ser Lys Ser Arg Ala Gly
610                 615                 620

Asp Thr Gly Val Lys Leu Glu Val Asn Glu Arg Ile Leu Gly Cys Cys
625                 630                 635                 640

Thr Ser Leu Met Gln Ala Ile Gln Val Leu Ile Val Ala Ser Lys Asp
                645                 650                 655

Leu Gln Arg Glu Ile Val Glu Ser Gly Arg Gly Thr Ala Ser Pro Lys
            660                 665                 670

Glu Phe Tyr Ala Lys Asn Ser Arg Trp Thr Glu Gly Leu Ile Ser Ala
        675                 680                 685

Ser Lys Ala Val Gly Trp Gly Ala Thr Val Met Val Asp Ala Ala Asp
    690                 695                 700

Leu Val Val Gln Gly Arg Gly Lys Phe Glu Glu Leu Met Val Cys Ser
705                 710                 715                 720

His Glu Ile Ala Ala Ser Thr Ala Gln Leu Val Ala Ala Ser Lys Val
                725                 730                 735

Lys Ala Asp Lys Asp Ser Pro Asn Leu Ala Gln Leu Gln Gln Ala Ser
            740                 745                 750

Arg Gly Val Asn Gln Ala Thr Ala Gly Val Val Ala Ser Thr Ile Ser
        755                 760                 765

Gly Lys Ser Gln Ile Glu Glu Thr Asp Asn Met Asp Phe Ser Ser Met
    770                 775                 780

Thr Leu Thr Gln Ile Lys Arg Gln Glu Met Asp Ser Gln Val Arg Val
785                 790                 795                 800

Leu Glu Leu Glu Asn Glu Leu Gln Lys Glu Arg Gln Lys Leu Gly Glu
```

-continued

```
               805                 810                 815
Leu Arg Lys Lys His Tyr Glu Leu Ala Gly Val Ala Glu Gly Trp Glu
           820                 825                 830
Glu Gly Thr Glu Ala Ser Pro Pro Thr Leu Gln Glu Val Val Thr Glu
           835                 840                 845
Lys Glu Ser Gln Thr Asn Thr Pro Tyr Val Ser Val Asn Pro Cys Tyr
           850                 855                 860
Leu Ser Arg Val Cys Tyr Phe Pro Ser His Arg Pro Asn Pro Trp Ser
865                    870                 875                 880
Pro Arg Gly Ser His Thr Thr Ala Ile Thr Gln Cys Arg Gly His Ala
               885                 890                 895
His Phe Gln Arg Leu Pro Pro Arg His Pro Phe Cys Leu Asp Pro Trp
           900                 905                 910
Ile Ser Thr Ala Ser Tyr Gly Gly Trp Leu Gly Phe Leu Val Leu Phe
           915                 920                 925
Phe Phe Phe Lys Phe His Ser His Ser Gln Leu Ser Gln Arg Ala His
           930                 935                 940
Pro Trp Gly Val Ser Arg Ala Pro Gln Leu Trp Leu Gln Arg Trp Cys
945                    950                 955                 960
Cys Pro Gly Leu Ser Val Leu His Leu Arg Leu His Thr Asp Gln Val
               965                 970                 975
Leu Ala His Pro Val His Ala Pro Gly Ser Gly Gly Ala Ala Glu Gln
               980                 985                 990
Leu Ser Ser Lys Ser Arg Arg Val Ser Ala Phe Pro Ser Ser Ile
           995                 1000                1005
Pro Ala Glu Ser Leu Cys Pro Pro Leu Gln Gly Arg Arg Gln Gln
           1010                1015                1020
Lys Glu Gly Gln Glu Gly Ser His Ser Pro Val Pro Val Thr Arg
           1025                1030                1035
Leu Lys Asn Leu Ile Thr Cys Leu Asn Gly Ala Gly Glu Ile Asn
           1040                1045                1050
Asn Thr Thr Ser Leu Pro Glu Thr Val Arg Glu Trp Ser Leu Ser
           1055                1060                1065
Ser Gly Pro Ser Pro Leu Ala Gln Arg Arg Ser Val Gly Val Ile
           1070                1075                1080
Pro Asn Ser Phe Leu Gln Thr Ser Ala Leu Ala Ser Ser Ile Gly
           1085                1090                1095
Arg Ser Phe His Leu Leu Arg Asn Gln Thr Arg Lys Ile Arg Cys
           1100                1105                1110
Asn Cys Ser His Gln Gly Arg Thr Leu Tyr Leu Val Cys Tyr Pro
           1115                1120                1125
Tyr Leu Leu Leu Thr Ser Leu Lys Gln Gln Gln Pro Thr Lys Arg
           1130                1135                1140
Cys Leu Glu Gln Ser Glu Leu Gln Val Leu Gln Ser Ser Ser Phe
           1145                1150                1155
Cys Pro Ala Thr Ser Ala Phe Lys Asn Gln Lys Lys Gly Gln Gly
           1160                1165                1170
Ala Gly Leu Leu Leu Thr Trp Ile Pro Lys Gln Gly Asp His Leu
           1175                1180                1185
Glu Leu Leu Gly Gln Arg Lys Glu Arg Thr Glu Pro Ala Ala Pro
           1190                1195                1200
Thr Pro Phe Ser His Met Pro Gln Ala Leu Ala Ala Leu Trp Thr
           1205                1210                1215
```

```
Gly Gly Gln Arg Ala His Glu     Gln Leu Ala Arg Asp     Gly Gln Pro
    1220                1225                1230

Asn Ser Thr Phe Pro Leu Leu     Asp Gly Pro Gln His     Leu Ser Asp
    1235                1240                1245

Leu Leu Ile Leu Gly Lys Gln     Arg Leu Pro Ser Leu     Ser Ile Ala
    1250                1255                1260

Thr His Trp Trp Pro Ser Ser     Thr Ser Glu Phe Leu     Gln Pro Gly
    1265                1270                1275

Arg Pro Leu Glu His
    1280

<210> SEQ ID NO 5
<211> LENGTH: 21
<212> TYPE: DNA
<213> ORGANISM: Homo sapiens

<400> SEQUENCE: 5
gctgtaaagg aaaaacacgc c                                          21

<210> SEQ ID NO 6
<211> LENGTH: 404
<212> TYPE: DNA
<213> ORGANISM: Homo sapiens

<400> SEQUENCE: 6
gggccgagcc agcggagggg ctcctgaagg ggcgggggcg ggcggggaag ccgttcggcg    60
aggggcgggg tctctggaag actggcagaa ctcacagcca atggcaggcg ggagccgtcc   120
cgttagcgcc ggatccccgc gggtagggcg gggcgggcgg cgccgtgggg atcccggggc   180
agccgagggc ccctgactcg gctcctcgcg gcgacatgga tcggatggcc agctccatga   240
agcaggtgcc caacccactg cccaaggtgc tgagccggcg cggggtcggc gctgggctgg   300
aggcggcgga gcgcgagagc ttcgagcgga ctcaggttca gactgtcagc atcaataagg   360
ccattaatac gcaggaaagt ggctgtaaag gaaaaacatg ccag                    404
```